United States Patent
Narula et al.

(10) Patent No.: US 10,696,606 B2
(45) Date of Patent: Jun. 30, 2020

(54) ZEOLITIC CATALYTIC CONVERSION OF ALCOHOLS TO HYDROCARBON FRACTIONS WITH REDUCED GASEOUS HYDROCARBON CONTENT

(71) Applicant: UT-BATTELLE, LLC, Oak Ridge, TN (US)

(72) Inventors: Chaitanya K. Narula, Knoxville, TN (US); Brian H. Davison, Knoxville, TN (US); Zhenglong Li, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 405 days.

(21) Appl. No.: 15/178,046

(22) Filed: Jun. 9, 2016

(65) Prior Publication Data

US 2017/0355649 A1    Dec. 14, 2017

(51) Int. Cl.
  *C10G 3/00* (2006.01)
  *C07C 1/20* (2006.01)
  (Continued)

(52) U.S. Cl.
  CPC ............ *C07C 1/20* (2013.01); *C07C 1/24* (2013.01); *C07C 2/12* (2013.01); *C07C 2/58* (2013.01);
  (Continued)

(58) Field of Classification Search
  None
  See application file for complete search history.

(56) References Cited

U.S. PATENT DOCUMENTS 3,702,886 A   11/1972   Argauer et al.
3,894,107 A   7/1975   Butter et al.
(Continued)

FOREIGN PATENT DOCUMENTS

CN   101454423 A   6/2009
EA   006785 B1   2/2005
(Continued)

OTHER PUBLICATIONS

Jurgen Schulz and Friedhelm Bandermann, Conversion of Ethanol over Metal-exchanged Zeolites, Chem. Eng. Technol. 16, 1993, pp. 332-337.
(Continued)

*Primary Examiner* — Philip Y Louie
(74) *Attorney, Agent, or Firm* — Scully, Scott, Murphy & Presser, P.C.

(57) ABSTRACT

A method for converting an alcohol to a hydrocarbon fraction reduced in gaseous hydrocarbon content, the method comprising: (i) contacting said alcohol with a metal-loaded zeolite catalyst under conditions suitable for converting said alcohol to a first hydrocarbon fraction containing liquid hydrocarbons having at least five carbon atoms along with gaseous hydrocarbons having less than five carbon atoms, wherein said metal-loaded zeolite catalyst is catalytically active for converting said alcohol to said first hydrocarbon fraction; and (ii) selectively removing said gaseous hydrocarbons from the first hydrocarbon fraction and contacting said gaseous hydrocarbons with a metal-loaded zeolite catalyst under conditions suitable for converting said gaseous hydrocarbons into liquid hydrocarbons having at least five carbon atoms to produce a second hydrocarbon fraction reduced in gaseous hydrocarbon content, wherein the metal-loaded zeolite catalyst in steps (i) and (ii) are the same or different.

14 Claims, 11 Drawing Sheets

(51) Int. Cl.
*B01J 29/48* (2006.01)
*C07C 1/24* (2006.01)
*C10G 50/00* (2006.01)
*C07C 2/12* (2006.01)
*C07C 2/58* (2006.01)
*C10L 1/04* (2006.01)
*C10L 1/06* (2006.01)
*C10L 1/08* (2006.01)

(52) U.S. Cl.
CPC ............... *C10G 3/45* (2013.01); *C10G 3/49* (2013.01); *C10G 50/00* (2013.01); *C10L 1/04* (2013.01); *C10L 1/06* (2013.01); *C10L 1/08* (2013.01); *C07C 2529/40* (2013.01); *C07C 2529/48* (2013.01); *C10G 2300/1014* (2013.01); *C10L 2200/043* (2013.01); *C10L 2200/0423* (2013.01); *C10L 2200/0446* (2013.01); *C10L 2200/0469* (2013.01); *C10L 2270/023* (2013.01); *C10L 2270/026* (2013.01); *C10L 2270/04* (2013.01); *C10L 2290/26* (2013.01); *Y02P 20/52* (2015.11)

(56) References Cited

U.S. PATENT DOCUMENTS

| | | |
|---|---|---|
| 3,899,544 A | 8/1975 | Chang et al. |
| 3,928,483 A | 12/1975 | Chang et al. |
| 3,931,349 A | 1/1976 | Kuo |
| 3,969,427 A | 7/1976 | Bell et al. |
| 3,998,899 A | 12/1976 | Daviduk et al. |
| 4,025,571 A | 5/1977 | Lago |
| 4,035,430 A | 7/1977 | Dwyer et al. |
| 4,058,576 A | 11/1977 | Chang et al. |
| 4,071,573 A | 1/1978 | Owen et al. |
| 4,138,440 A | 2/1979 | Chang et al. |
| 4,148,835 A | 4/1979 | Chen et al. |
| 4,216,346 A | 8/1980 | Antos |
| 4,278,565 A | 7/1981 | Chen et al. |
| 4,289,606 A | 9/1981 | Gladrow et al. |
| 4,338,475 A | 7/1982 | Pennington et al. |
| 4,404,414 A | 9/1983 | Penick et al. |
| 4,423,274 A | 12/1983 | Daviduk et al. |
| 4,427,789 A | 1/1984 | Miale et al. |
| 4,499,327 A | 2/1985 | Kaiser |
| 4,524,234 A | 6/1985 | Kaiser |
| 4,596,704 A | 6/1986 | Miale et al. |
| 4,608,355 A | 8/1986 | Chu |
| 4,690,903 A * | 9/1987 | Chen ............... C07C 29/76 435/161 |
| 4,727,214 A | 2/1988 | Uytterhoeven et al. |
| 4,788,042 A | 11/1988 | Marsh et al. |
| 4,788,369 A | 11/1988 | Marsh et al. |
| 4,849,093 A | 7/1989 | Vauk et al. |
| 4,851,606 A * | 7/1989 | Ragonese ............ C07C 1/20 210/774 |
| 4,861,937 A | 8/1989 | Baacke et al. |
| 4,899,015 A * | 2/1990 | Harandi ............... C07C 2/12 585/520 |
| 5,041,690 A | 8/1991 | Harandi et al. |
| 5,045,287 A | 9/1991 | Harandi et al. |
| 5,047,070 A | 9/1991 | Harandi et al. |
| 5,177,279 A | 1/1993 | Harandi |
| 5,491,270 A | 2/1996 | Chin et al. |
| 5,773,676 A | 6/1998 | Drake et al. |
| 6,046,373 A | 4/2000 | Sun |
| 6,323,383 B1 | 11/2001 | Tsuchida et al. |
| 6,426,442 B1 | 7/2002 | Ichikawa et al. |
| 7,872,054 B2 | 1/2011 | Cortright et al. |
| 9,181,493 B2 * | 11/2015 | Narula ............... C10G 3/00 |
| 9,278,892 B2 | 3/2016 | Narula et al. |
| 9,533,921 B2 * | 1/2017 | Narula ............... C10G 3/45 |
| 9,938,467 B2 * | 4/2018 | Narula ............... C10G 3/45 |
| 2003/0171630 A1 | 9/2003 | Winder et al. |
| 2007/0087934 A1 | 4/2007 | Martens et al. |
| 2008/0103345 A1 | 5/2008 | Levin et al. |
| 2008/0287720 A1 | 11/2008 | Clark |
| 2010/0185033 A1 | 7/2010 | Karim et al. |
| 2010/0304455 A1 | 12/2010 | Inoue et al. |
| 2011/0047864 A1 | 3/2011 | Bhan et al. |
| 2011/0061290 A1 | 3/2011 | Aulich et al. |
| 2011/0152513 A1 | 6/2011 | Yao et al. |
| 2012/0004481 A1 | 1/2012 | Guillon et al. |
| 2013/0217935 A1 | 8/2013 | Adam et al. |
| 2014/0100404 A1 | 4/2014 | Narula et al. |
| 2014/0148630 A1 | 5/2014 | Adam et al. |
| 2014/0171691 A1 | 6/2014 | Kortan et al. |
| 2014/0273146 A1 | 9/2014 | Narula et al. |
| 2015/0011813 A1 | 1/2015 | Narula et al. |
| 2016/0332195 A1 | 11/2016 | Li et al. |

FOREIGN PATENT DOCUMENTS

| | | |
|---|---|---|
| EA | 015812 B1 | 12/2008 |
| EP | 0099650 | 2/1984 |
| EP | 0130368 | 1/1985 |
| RU | 2 082 500 C1 | 6/1997 |
| RU | 98121148 A | 10/2000 |
| RU | 2 407 778 C2 | 1/2010 |
| WO | WO 90/12855 | 11/1990 |
| WO | WO 2007/020068 A1 | 2/2007 |
| WO | WO 2007/112314 A2 | 10/2007 |
| WO | WO 2008/069841 A2 | 6/2008 |
| WO | WO 2008/069984 A2 | 6/2008 |
| WO | WO 2012/016787 A1 | 2/2012 |
| WO | WO 2012/174205 A1 | 12/2012 |
| WO | WO 2013-014081 A1 | 1/2013 |
| WO | WO 2016/116612 A1 | 7/2016 |

OTHER PUBLICATIONS

International Search Report and Written Opinion dated Sep. 8, 2017 issued in PCT/US17/36786.

* cited by examiner ures, such as use of an elevated pressure during the process. However, the efforts thus far considered have the drawback of either requiring specialized conditions that are costly or would be a challenge to adopt on a commercial scale, or they are generally not widely applicable to a range of catalysts and alcohols. A process that is more amenable to commercial scale-up and more widely applicable to a range of catalysts, alcohol-containing starting materials, and process conditions would be a significant advance in the catalytic conversion of alcohols to hydrocarbons.

ZEOLITIC CATALYTIC CONVERSION OF ALCOHOLS TO HYDROCARBON FRACTIONS WITH REDUCED GASEOUS HYDROCARBON CONTENT

This invention was made with government support under Prime Contract No. DE-AC05-00OR22725 awarded by the U.S. Department of Energy. The government has certain rights in the invention.

FIELD OF THE INVENTION

The present invention relates, generally, to the catalytic conversion of alcohols to hydrocarbons, and more particularly, to zeolite-based catalytic methods for such conversion.

BACKGROUND OF THE INVENTION

As part of a continuing effort in finding more cost effective, environmentally friendly, and independent solutions to fuel production and consumption, the conversion of ethanol and other alcohols to hydrocarbons has become an active field of study. Ethanol is of primary interest as an alcohol feedstock because it has the potential to be made in large quantity by renewable means (e.g., fermentation of biomass). However, several hurdles need to be overcome before such a process can become industrially feasible for producing hydrocarbon blendstocks of substantial equivalence to gasoline and other petrochemical fuels.

A particular drawback in the use of ethanol in catalytic conversion is its tendency to produce a significant quantity of ethylene and other gaseous hydrocarbons. Gaseous hydrocarbons are generally an undesirable component in a hydrocarbon fuel. A hydrocarbon fuel is more preferably composed predominantly of liquid hydrocarbons, with the gaseous hydrocarbon fraction minimized to the extent possible.

Thus, there have been continued efforts in reducing the gaseous hydrocarbon fraction in alcohol conversion processes of the art. Some of these efforts rely on careful selection of the catalyst, careful selection of the alcohol, and/or careful selection of the conversion conditions, such as use of an elevated pressure during the process. However, the efforts thus far considered have the drawback of either requiring specialized conditions that are costly or would be a challenge to adopt on a commercial scale, or they are generally not widely applicable to a range of catalysts and alcohols. A process that is more amenable to commercial scale-up and more widely applicable to a range of catalysts, alcohol-containing starting materials, and process conditions would be a significant advance in the catalytic conversion of alcohols to hydrocarbons.

SUMMARY OF THE INVENTION

The present disclosure is directed to an alcohol-to-hydrocarbon catalytic conversion method that advantageously produces a hydrocarbon fraction (i.e., hydrocarbon blendstock) having a reduced level of gaseous hydrocarbons and greater relative amount of liquid hydrocarbons. Generally, the gaseous hydrocarbons have less than five carbon atoms, such as methane, ethylene, ethane, propene, propane, isobutane, 2-butene, butane, and isobutylene. The resulting blendstock, reduced in such gaseous hydrocarbons, is advantageously significantly more enriched in liquid hydrocarbons, which generally have at least five carbon atoms. The invention accomplishes this by catalytically converting at least one alcohol to produce a hydrocarbon fraction containing liquid and gaseous hydrocarbons, selectively removing the gaseous hydrocarbon fraction, and further processing the gaseous hydrocarbon fraction to convert gaseous hydrocarbon species in the gaseous fraction to higher liquid hydrocarbon species. The resulting hydrocarbon blendstock may be used directly as a fuel, or in other embodiments, may be mixed with another hydrocarbon blendstock or fuel (e.g., straight run or reformate gasoline) or may be further processed to suitably adjust the composition of the final blendstock in any desired characteristics, such as olefin content, aromatics content, or octane rating.

More particularly, the invention includes: (i) contacting an alcohol with a metal-loaded zeolite catalyst under conditions suitable for converting the alcohol to a first hydrocarbon fraction containing liquid hydrocarbons having at least five carbon atoms along with gaseous hydrocarbons having less than five carbon atoms, wherein the metal-loaded zeolite catalyst is catalytically active for converting the alcohol to the first hydrocarbon fraction; and (ii) selectively removing the gaseous hydrocarbons from the first hydrocarbon fraction and contacting the gaseous hydrocarbons with a metal-loaded zeolite catalyst under conditions suitable for converting the gaseous hydrocarbons into liquid hydrocarbons having at least five carbon atoms to produce a second or subsequent hydrocarbon fraction reduced in gaseous hydrocarbon content, wherein the metal-loaded zeolite catalyst in steps (i) and (ii) are the same or different.

The process can furthermore be practiced as a single-zone (recirculation, or one-step) process or a two-zone (two-step) process. In the single-zone process, gaseous hydrocarbons in step (ii) are recirculated back to the metal-loaded zeolite catalyst used in step (i) while the metal-loaded zeolite catalyst continues to convert the alcohol to the first hydrocarbon fraction. Thus, by the single-zone process, recirculated gaseous hydrocarbon species are converted into higher liquid hydrocarbon species simultaneous with continued production of liquid and additional gaseous hydrocarbon species, the latter of which are again and continuously recirculated back to the zone in which alcohol-to-hydrocarbon conversion continues to occur. In contrast, in the two-zone process, step (i) is conducted in a first zone containing a first metal-loaded zeolite catalyst, and the gaseous hydrocarbons selectively removed from the hydrocarbon fraction produced in step (i) are transported in step (ii) from the first zone to a second zone in which the gaseous hydrocarbons are contacted with a second metal-loaded zeolite catalyst under conditions suitable for converting the gaseous hydrocarbons into liquid hydrocarbons having at least five carbon atoms.

The processes described above are advantageously straightforward, more amenable to commercial scale-up, and more widely applicable to a range of catalysts, alcohols, and process conditions than conventional processes of the art. Moreover, by methods described herein, the alcohol being used as a conversion substrate is essentially unlimited, and the alcohol need not even be concentrated or dry. Indeed, by using the methods described herein, effective conversion can be accomplished on aqueous solutions of an alcohol, and even dilute aqueous solutions, such as found in the fermentation stream of a biomass fermentation reactor. In different embodiments, the aqueous solution of alcohol can have a high concentration of alcohol (e.g., pure alcohol, or alcohol concentration of over 50%), a moderate concentration of alcohol (e.g., at least 20% and up to 30%, 40%, or 50%), or a low concentration of alcohol (e.g., up to or less than 20%, 10%, or 5%). The ability of the described method to convert aqueous solutions of alcohol is particularly advantageous since concentration and/or distillation of alcohol from a fermentation stream (as often practiced in the conventional art) is highly energy intensive and largely offsets gains made in the initial low cost of using a bio-alcohol.

BRIEF DESCRIPTION OF THE DRAWINGS

FIGS. 4A, 4B, and 4C are graphs plotting liquid composition (%) vs. time on stream (TOS) in hours at 10 ccm, 20 ccm, and 40 ccm, respectively, of light gas co-feeding with 0.2 g V-ZSM-5 catalyst and 0.4 mL/h ethanol flow at 359° C. catalyst temperature.

FIGS. 6A, 6B, and 6C are graphs plotting conversions (%) for ethylene, propene, and propane at 10 ccm (FIG. 6A), 20 ccm (FIG. 6B), and 40 ccm (FIG. 6C) light gas co-feeding using 0.2 g V-ZSM-5 catalyst and 0.4 mL/h ethanol flow at 359° C. catalyst temperature.

FIGS. 8A, 8B, and 8C are graphs plotting conversions (%) for isobutylene and 2-butene at 10 ccm (FIG. 8A), 20 ccm (FIG. 8B), and 40 ccm (FIG. 8C) light gas co-feeding using 0.2 g V-ZSM-5 catalyst and 0.4 mL/h ethanol flow at 359° C. catalyst temperature.

FIG. 10A is a graph plotting liquid composition in terms of relative amounts of paraffins, olefin, and aromatics vs. light gas mixture flow rate (ccm) using 0.2 g V-ZSM-5 catalyst at 359° C. catalyst temperature and no ethanol co-feeding.

FIG. 10B is a graph plotting benzene concentration vs. light gas mixture flow rate (ccm) using 0.2 g V-ZSM-5 catalyst at 359° C. catalyst temperature and no ethanol co-feeding.

FIG. 11A is a graph plotting extent of conversion of ethylene, propene, propane, 2-butene, and isobutylene to liquid hydrocarbons (%) vs. light gas mixture flow rate (ccm) using 0.2 g V-ZSM-5 catalyst at 359° C. catalyst temperature and no ethanol co-feeding. FIG. 11B is a graph plotting extent of conversion of isobutane to liquid hydrocarbons (%) vs. light gas mixture flow rate (ccm) using 0.2 g V-ZSM-5 catalyst at 359° C. catalyst temperature and no ethanol co-feeding.

DETAILED DESCRIPTION OF THE INVENTION

Figure 1:
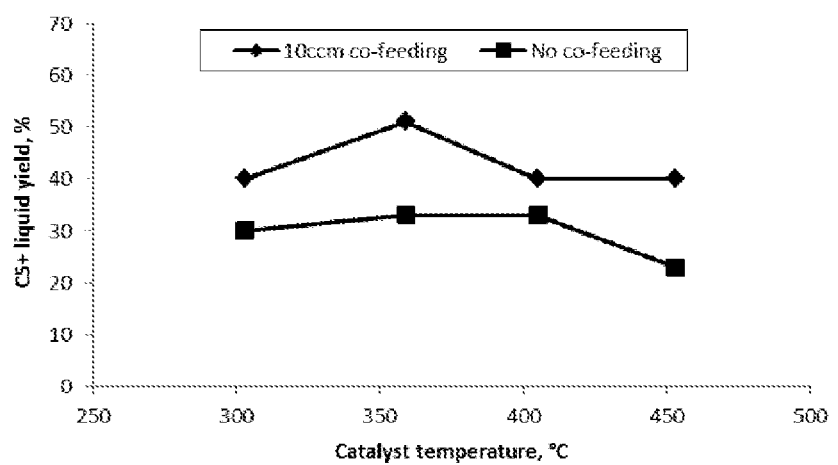
FIG. 1. Graph plotting liquid hydrocarbon yield ($C_5^+$) at different catalyst temperatures with 0.2 g V-ZSM-5 and 0.4 mL/h ethanol feed, and either co-feeding at 10 ccm flow rate of a light gas mixture, or no co-feeding of a light gas mixture.

In the conversion method described herein, an alcohol is catalytically converted to a hydrocarbon fraction by contacting the alcohol with a metal-loaded zeolite catalyst at conditions (particularly, temperature and choice of catalyst) suitable to effect said conversion. As used herein, the term "alcohol" is meant to include a single alcohol or a mixture of two or more alcohols. The term "hydrocarbon fraction," without additional qualifiers, refers to a mixture (i.e., blendstock) of hydrocarbon compounds, at least a portion of which are liquid hydrocarbons having at least five carbon atoms (i.e., "$C_5^+$ hydrocarbons"). The term "liquid hydrocarbon fraction" refers to a sub-fraction of the hydrocarbon fraction that is composed of liquid hydrocarbons. The term "gaseous hydrocarbon fraction" refers to a sub-fraction of the hydrocarbon fraction that is composed of gaseous hydrocarbons, typically those hydrocarbons having less than five carbon atoms, and predominantly those having two to four carbons atoms (i.e., "$C_2$-$C_4$ hydrocarbons"). As used herein, the term "hydrocarbons" is synonymous with the term "hydrocarbon compounds".

The alcohol considered herein is generally of the formula R—OH, where R is typically a straight-chained or branched alkyl group having at least one or two carbon atoms and up to any number of carbon atoms, e.g., up to 10, 12, 15, 18, or 20 carbon atoms, but more typically, up to three or four carbon atoms. The alcohol is typically a primary or secondary alcohol. Some examples of suitable alcohols include methanol, ethanol, n-propanol, isopropanol, n-butanol, isobutanol, sec-butanol, tert-butanol, n-pentanol, and isopentanol. As alcohols containing more than three carbon atoms generally produce a lower amount of gaseous hydrocarbons upon conversion, the present disclosure is primarily directed to conversion of alcohol starting materials containing some amount of ethanol and/or methanol. In some embodiments, the alcohol starting material contains an absence of any one or more alcohols other than ethanol, such as an absence of any one or more of the alcohols provided above other than ethanol.

The alcohol can be in any concentration, including pure (dry) alcohol, i.e., at or about 100%. In some embodiments, the alcohol considered herein, to be converted to hydrocarbon, is one that can be produced by a fermentation process (i.e., a bio-alcohol). Most notable examples of bio-alcohols considered herein include ethanol, n-butanol (i.e., butanol), and isobutanol. In different embodiments, the alcohol can be ethanol, or butanol, or isobutanol, or a combination thereof, as commonly found in fermentation streams. In particular embodiments, the alcohol is an aqueous solution of alcohol (i.e., the alcohol is a component of an aqueous solution), as found in fermentation streams. In fermentation streams, the alcohol is typically in a concentration of no more than about 20% (vol/vol), 15%, 10%, or 5%, wherein the term "about" generally indicates within ±0.5%, 1%, 2%, 5%, or up to ±10% of the indicated value. In some embodiments, a fermentation stream or other alcoholic aqueous solution is directly contacted with the catalyst (typically, after filtration to remove solids) to effect the conversion of the alcohol in the fermentation stream. In other embodiments, the fermentation stream or other alcoholic aqueous solution is concentrated in alcohol (for example, of at least or up to 20%, 30%, 40%, or 50%) before contacting the fermentation stream with the catalyst. In yet other embodiments, alcohol in the fermentation stream or other alcoholic aqueous solution is selectively removed from the alcoholic aqueous solution, such as by distillation, to produce a substantially pure form of alcohol as the feedstock (e.g., a concentration of at least 90% or 95% of alcohol). In still other embodiments, the alcohol is completely dewatered into 100% alcohol before contacting with the catalyst.

The liquid hydrocarbon fraction produced by the instant process generally includes a saturated (alkane or paraffin) portion. The paraffins may be straight-chained, branched, or cyclic, and generally include a mixture thereof. The liquid paraffins are typically those containing at least five or six carbon atoms, and up to, for example, 10, 12, 15, 18, or 20 carbon atoms. Some examples of straight-chained paraffins include n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, and n-eicosane. Some examples of branched paraffins include isopentane, neopentane, isohexane, 3-methylpentane, 2,3-dimethylbutane, 2,2-dimethylbutane, 2-methylhexane, 3-methylhexane, 2,2-dimethylpentane, 2,3-dimethylpentane, 2,4-dimethylpentane, 3,3-dimethylpentane, 2-methylheptane, 2,2,4-trimethylpentane (isooctane), isononane, and isodecane. Some examples of cyclic paraffins include cyclopropane, cyclobutane, cyclopentane, and cyclohexane.

The liquid hydrocarbon fraction may also include an olefin portion. Some examples of straight-chained and branched olefins that may constitute the olefin portion include 1-pentene, cis-2-pentene, trans-2-pentene, isopentene (3-methyl-1-butene), 1,3-pentadiene, 1-hexene, cis-2-hexene, trans-2-hexene, cis-3-hexene, trans-3-hexene, isohexene (4-methyl-1-pentene), 3-methyl-1-pentene, 3,4-dimethyl-1-pentene, 1,5-hexadiene, 2,4-hexadiene, 1-heptene, isoheptene (5-methyl-1-hexene), 4-methyl-1-hexene, 1-octene, 2,4,4-trimethyl-1-pentene, 1-nonene, and 1-decene. The liquid hydrocarbon fraction may also include an aromatic portion, which may be in a predominant or minor amount in the hydrocarbon fraction. Some examples of aromatic compounds that may constitute the aromatic portion include benzene, toluene, xylenes, trimethylbenzenes, ethylbenzenes, and naphthalene.

The hydrocarbon product (fraction) particularly considered herein is a mixture of hydrocarbon compounds useful as a fuel or as a blendstock in fuel. The mixture of hydrocarbon compounds produced herein preferably substantially corresponds (e.g., in composition and/or properties) to a known petrochemical fuel, such as petroleum, or a fractional distillate of petroleum. Some examples of petrochemical fuels include gasoline, kerosene, diesel, and jet propellant (e.g., JP-8). Like hydrocarbon fuel grades in current use, the mixture of hydrocarbon compounds produced herein can, in some embodiments, be predominantly or exclusively composed of alkanes, alkenes, aromatics, or a mixture thereof. Although aromatics (particularly benzene) may be present in the hydrocarbon mixture, their presence may be minimized to adhere to current fuel standards, such as by contacting the produced hydrocarbon fraction with a benzene alkylation catalyst, under conditions suitable for alkylating benzene, to form alkylated benzene product in the hydrocarbon fraction (as discussed in, e.g., U.S. Pat. No. 9,278,892, the contents of which are herein incorporated by reference).

The raw hydrocarbon product, produced by the instantly described method, is typically fractionated by distillation into different fuel grades, each of which is known to be within a certain boiling point range. A particular advantage of the instant method is its ability to produce such fuel grades in the substantial absence of contaminants (e.g., mercaptans) normally required to be removed during the petroleum refining process. Moreover, by appropriate adjustment of the catalyst and processing conditions, a select distribution of hydrocarbons can be obtained. In particular, as further discussed in the Examples, a surprising effect of the described method, in which gaseous hydrocarbons are selectively removed and re-processed to form additional liquid hydrocarbons, is its ability to reduce the benzene content to levels below regulatory limits, e.g., up to or below 5%, 4%, 3%, 2%, 1%, 0.68% (EPA regulatory limit), 0.5%, 0.4%, 0.3%, 0.2%, or 0.1%.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers. The process provides this level of versatility by appropriate selection of, for example, composition of the catalyst (e.g., catalytic metal), amount of catalyst (e.g., ratio of catalyst to alcohol precursor), processing temperature, and flow rate (e.g., LHSV).

In the process, a suitable reaction temperature is employed during contact of the alcohol with the catalyst. Generally, the reaction temperature is at least 100° C. and up to 550° C. In different embodiments, the reaction is precisely or about, for example, 100° C., 125° C., 150° C., 175° C., 200° C., 225° C., 250° C., 275° C., 300° C., 325° C., 350° C., 375° C., 400° C., 425° C., 450° C., 475° C., 500° C., 525° C., or 550° C., or a temperature within a range bounded by any two of the foregoing exemplary temperatures (e.g., 100° C.-550° C., 200° C.-550° C., 300° C.-550° C., 400° C.-550° C., 450° C.-550° C., 100° C.-500° C., 200° C.-500° C., 300° C.-500° C., 350° C.-500° C., 400° C.-500° C., 450° C.-500° C., 100° C.-450° C., 200° C.-450° C., 300° C.-450° C., 350° C.-450° C., 400° C.-450° C., 100° C.-425° C., 200° C.-425° C., 300° C.-425° C., 350° C.-425° C., 375° C.-425° C., 400° C.-425° C., 100° C.-400° C., 200° C.-400° C., 300° C.-400° C., 350° C.-400° C., and 375° C.-400° C.).

Generally, ambient (i.e., normal atmospheric) pressure of about 1 atm is used in the method described herein. However, in some embodiments, an elevated pressure or reduced pressure may be used. For example, in some embodiments, the pressure may be elevated to, for example, 1.5, 2, 3, 4, or 5 atm, or reduced to, for example, 0.5, 0.2, or 0.1 atm.

The catalyst and reactor can have any of the designs known in the art for catalytically treating a fluid or gas at elevated temperatures, such as a fluidized bed reactor. The process may be in a continuous or batch mode. In particular embodiments, the alcohol is injected into a heated reactor such that the alcohol is quickly volatilized into gas, and the gas passed over the catalyst. In some embodiments, the reactor design includes a boiler unit and a reactor unit if the fermentation stream is used directly as a feedstock without purification. The boiler unit is generally not needed if the fermentation stream is distilled to concentrate ethanol because the distillation process removes the dissolved solids in the fermentation streams. The boiler unit volatilizes liquid feedstock into gases prior to entry into the reactor unit and withholds dissolved solids.

The conversion catalyst used herein includes a zeolite portion and a metal loaded into the zeolite. The zeolite considered herein can be any of the porous aluminosilicate structures known in the art that are stable under high temperature conditions, i.e., of at least 100° C., 150° C., 200° C., 250° C., 300° C., and higher temperatures up to, for example, 500° C., 550° C., 600° C., 650° C., 700° C., 750° C., 800° C., 850° C., or 900° C. In particular embodiments, the zeolite is stable from at least 100° C. and up to 700° C. Typically, the zeolite is ordered by having a crystalline or partly crystalline structure. The zeolite can generally be described as a three-dimensional framework containing silicate ($SiO_2$ or $SiO_4$) and aluminate ($Al_2O_3$ or $AlO_4$) units that are interconnected (i.e., crosslinked) by the sharing of oxygen atoms.

The zeolite can be microporous (i.e., pore size of less than 2 nm), mesoporous (i.e., pore size within 2-50 nm, or sub-range therein), or a combination thereof. In several embodiments, the zeolite material is completely or substantially microporous. By being completely or substantially microporous, the pore volume due to micropores can be, for example, 100%, or at least 95%, 96%, 97%, 98%, 99%, or 99.5%, with the remaining pore volume being due to mesopores, or in some embodiments, macropores (pore size greater than 50 nm). In other embodiments, the zeolite material is completely or substantially mesoporous. By being completely or substantially mesoporous, the pore volume due to mesopores can be, for example, 100%, or at least 95%, 96%, 97%, 98%, 99%, or 99.5%, with the remaining pore volume being due to micropores, or in some embodiments, macropores. In yet other embodiments, the zeolite material contains an abundance of both micropores and mesopores. By containing an abundance of both micropores and mesopores, the pore volume due to mesopores can be, for example, up to, at least, or precisely 50%, 60%, 70%, 80%, or 90%, with the pore volume balance being due to micropores, or vice-versa.

In various embodiments, the zeolite is a MFI-type zeolite, MEL-type zeolite, MTW-type zeolite, MCM-type zeolite, BEA-type zeolite, kaolin, or a faujasite-type of zeolite. Some particular examples of zeolites include the ZSM class of zeolites (e.g., ZSM-5, ZSM-8, ZSM-11, ZSM-12, ZSM-15, ZSM-23, ZSM-35, ZSM-38, ZSM-48), zeolite X, zeolite Y, zeolite beta, and the MCM class of zeolites (e.g., MCM-22 and MCM-49). The compositions, structures, and properties of these zeolites are well-known in the art, and have been described in detail, as found in, for example, U.S. Pat. Nos. 4,721,609, 4,596,704, 3,702,886, 7,459,413, and 4,427,789, the contents of which are incorporated herein by reference in their entirety. In some embodiments, any one or more of the above-described zeolites may be excluded as a conversion catalyst in the process described above or as further described below.

The zeolite can have any suitable silica-to-alumina (i.e., $SiO_2/Al_2O_3$ or "Si/Al") ratio. For example, in various embodiments, the zeolite can have a Si/Al ratio of precisely, at least, less than, or up to 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 120, 150, 200, 300, or 400, or a Si/Al ratio within a range bounded by any two of the foregoing values. In particular embodiments, the zeolite possesses a Si/Al ratio of 1 to 45.

In particular embodiments, the zeolite is ZSM-5. ZSM-5 belongs to the pentasil-containing class of zeolites, all of which are also considered herein. In particular embodiments, the ZSM-5 zeolite is represented by the formula $Na_nAl_nSi_{96-n}O_{192} \cdot 16H_2O$, wherein $0<n<27$.

Typically, the zeolite contains an amount of cationic species. As is well known in the art, the amount of cationic species is generally proportional to the amount of aluminum in the zeolite. This is because the replacement of silicon atoms with lower valent aluminum atoms necessitates the presence of countercations to establish a charge balance. Some examples of cationic species include hydrogen ions ($H^+$), alkali metal ions, alkaline earth metal ions, and main group metal ions. Some examples of alkali metal ions that may be included in the zeolite include lithium ($Li^+$), sodium ($Na^+$), potassium ($K^+$), rubidium ($Rb^+$), and cesium ($Cs^+$). Some examples of alkaline earth metal ions that may be included in the zeolite include ($Be^{2+}$), magnesium ($Me^+$), calcium ($Ca^{2+}$), strontium ($Sr^{2+}$), and barium ($Ba^{2+}$). Some examples of main group metal ions that may be included in the zeolite include boron ($B^{3+}$), gallium ($Ga^{3+}$), indium ($In^{3+}$), and arsenic ($As^{3+}$). In some embodiments, a combination of cationic species is included. The cationic species can be in a trace amount (e.g., no more than 0.01 or 0.001%), or alternatively, in a significant amount (e.g., above 0.01%, and up to, for example, 0.1, 0.5, 1, 2, 3, 4, or 5% by weight of the zeolite). In some embodiments, any one or more of the above classes or specific examples of cationic species are excluded from the zeolite.

The zeolite described above is loaded with an amount of metal. The metal loaded into the zeolite is selected such that the resulting metal-loaded zeolite is catalytically active, under conditions set forth above, for converting an alcohol to a hydrocarbon. As further discussed below, the metal-loaded zeolite may alternatively, or in addition, be catalytically active for converting gaseous hydrocarbons to liquid hydrocarbons under suitable conditions, which may be the same or different than the conditions set forth above for converting an alcohol to hydrocarbons. Typically, the metal considered herein is in the form of positively-charged metal ions (i.e., metal cations). The metal cations can be, for example, monovalent, divalent, trivalent, tetravalent, pentavalent, or hexavalent. In some embodiments, the metal is (or includes) alkali metal ions. In other embodiments, the metal is (or includes) alkaline earth metal ions. In other embodiments, the metal is (or includes) a transition metal, such as one or more first, second, or third row transition metals. Some preferred transition metals include copper, iron, zinc, titanium, vanadium, and cadmium. The copper ions can be cuprous ($Cu^{+1}$) or cupric ($Cu^{+2}$) in nature, and the iron atoms can be ferrous ($Fe^{+2}$) or ferric ($Fe^{+3}$) in nature. Vanadium ions may be in any of its known oxidation states, e.g., $V^{+2}$, $V^{+3}$, $V^{+4}$, and $V^{+5}$. In other embodiments, the metal is (or includes) a catalytically active main group metal, such as gallium or indium. A single metal or a combination of metals may be loaded into the zeolite. In other embodiments, any one or more metals described above are excluded from the zeolite.

The metal loading can be any suitable amount, but is generally no more than about 2.5%, wherein the loading is expressed as the amount of metal by weight of the zeolite. In different embodiments, the metal loading is precisely, at least, less than, or up to, for example, 0.01%, 0.02%, 0.03%, 0.04%, 0.05%, 0.06%, 0.07%, 0.08%, 0.09%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 3.0%, 4.0%, 5.0%, 6.0%, 7.0%, 8.0%, 9.0%, or 10%, or a metal loading within a range bounded by any two of the foregoing values.

In some embodiments, the zeolite catalyst may include at least one trivalent metal ion. As used herein, the term "trivalent metal ion" is defined as a trivalent metal ion other than aluminum ($Al^{+3}$). Without wishing to be bound by any theory, it is believed that the trivalent metal is incorporated into the zeolite structure. More specifically, the incorporated trivalent metal ion is believed to be bound in the zeolite to an appropriate number of oxygen atoms, i.e., as a metal oxide unit containing the metal cation connected to the structure via oxygen bridges. In some embodiments, the presence of a trivalent metal ion in combination with one or more other catalytically active metal ions may result in a synergistic effect compared to the cumulative effect of these ions when used individually. The effect primarily considered herein is on the resulting catalyst's ability to convert alcohols into hydrocarbons.

In some embodiments, only one type of trivalent metal ion aside from aluminum is incorporated into the zeolite. In other embodiments, at least two types of trivalent metal ions aside from aluminum are incorporated into the zeolite. In yet other embodiments, at least three types of trivalent metal ions aside from aluminum are incorporated into the zeolite.

Each of the trivalent metal ions can be included in any suitable amount, such as, precisely, at least, less than, or up to, for example, 0.01%, 0.02%, 0.03%, 0.04%, 0.05%, 0.06%, 0.07%, 0.08%, 0.09%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 3.0%, 4.0%, 5.0%, 6.0%, 7.0%, 8.0%, 9.0%, or 10%, or an amount within a range bounded by any two of the foregoing values. Alternatively, the total amount of trivalent metal ions (other than Al) may be limited to any of the foregoing values.

In a first set of embodiments, at least one trivalent metal ion is selected from trivalent transition metal ions. The one or more transition metals can be selected from any or a select portion of the following types of transition metals: elements of Groups IIIB (Sc group), IVB (Ti group), VB (V group), VIB (Cr group), VIIB (Mn group), VIIIB (Fe and Co groups) of the Periodic Table of the Elements. Some examples of trivalent transition metal ions include $Sc^{+3}$, $Y^{+3}$, $V^{+3}$, $Nb^{+3}$, $Cr^{+3}$, $Fe^{+3}$, and $Co^{+3}$. In other embodiments, the trivalent metal ion excludes all transition metal ions, or alternatively, excludes any one, two, or more classes or specific examples of transition metal ions provided above. In particular embodiments, the trivalent transition metal ions include $Sc^{+3}$, or $Fe^{+3}$, or $V^{+3}$, or $Cr^{+3}$, or a combination thereof. Any of the foregoing trivalent transition metal ions may also be combined with one or more divalent metal ions, such as an alkaline earth metal ion, $Cu^{+2}$, $V^{+2}$, $Cr^{+2}$, $Mn^{+2}$, $Fe^{+2}$, $Co^{+2}$, $Ni^{+2}$, $Zn^{+2}$, or $Cd^{+2}$.

In a second set of embodiments, at least one trivalent metal ion is selected from trivalent main group metal ions. The one or more main group metals can be selected from any or a select portion of elements of Group IIIA (boron group) and/or Group VA (nitrogen group) of the Periodic Table, other than aluminum. Some examples of trivalent main group metal ions include $Ga^{+3}$, $In^{+3}$, $As^{+3}$, $Sb^{+3}$, and $Bi^{+3}$. In other embodiments, the trivalent metal ion excludes all main group metal ions other than aluminum, or alternatively, excludes any one, two, or more classes or specific examples of main group metal ions provided above. In particular embodiments, the trivalent main group metal ions include at least $Ga^{+3}$ and/or $In^{3+}$. Any of the foregoing trivalent main group metal ions may also be combined with one or more divalent metal ions, such as an alkaline earth metal ion, $Cu^{+2}$, $V^{+2}$, $Cr^{+2}$, $Mn^{+2}$, $Fe^{+2}$, $Co^{+2}$, $Ni^{+2}$, $Zn^{+2}$, or $Cd^{+2}$.

In a third set of embodiments, at least one trivalent metal ion is selected from trivalent lanthanide metal ions. Some examples of trivalent lanthanide metal ions considered herein include $La^{+3}$, $Ce^{+3}$, $Pr^{+3}$, $Nd^{+3}$, $Sm^{+3}$, $Eu^{+3}$, $Gd^{+3}$, $Tb^{+3}$, $Dy^{+3}$, $Ho^{+3}$, $Er^{+3}$, $Tm^{+3}$, $Yb^{+3}$, and $Lu^{+3}$. In particular embodiments, the trivalent lanthanide metal ion is selected from one or a combination of $La^{+3}$, $Ce^{+3}$, $Pr^{+3}$, and $Nd^{+3}$. In further particular embodiments, the trivalent lanthanide metal ion is or includes $La^{+3}$. In other embodiments, the trivalent metal ion excludes all lanthanide metal ions, or alternatively, excludes any one, two, or more classes or specific examples of lanthanide metal ions provided above.

In a fourth set of embodiments, the catalyst includes at least two trivalent metal ions selected from trivalent transition metal ions. Some combinations of trivalent transition metal ions considered herein include $Sc^{+3}$ in combination with one or more other trivalent transition metal ions, or $Fe^{+3}$ in combination with one or more other trivalent transition metal ions, or $Y^{+3}$ in combination with one or more other trivalent transition metal ions, or $V^{+3}$ in combination with one or more other trivalent transition metal ions, or $Cr^{+3}$ in combination with one or more other trivalent transition metal ions.

In a fifth set of embodiments, the catalyst includes at least two trivalent metal ions selected from trivalent main group metal ions. Some combinations of trivalent main group metal ions considered herein include $In^{+3}$ in combination with one or more other trivalent main group metal ions, or $Ga^{+3}$ in combination with one or more other trivalent main group metal ions, or $As^{+3}$ in combination with one or more other trivalent main group metal ions.

In a sixth set of embodiments, the catalyst includes at least two trivalent metal ions selected from trivalent lanthanide metal ions. Some combinations of trivalent lanthanide metal ions considered herein include $La^{+3}$ in combination with one or more other trivalent lanthanide metal ions, or $Ce^{+3}$ in combination with one or more other trivalent lanthanide metal ions, or $Pr^{+3}$ in combination with one or more other trivalent lanthanide metal ions, or $Nd^{+3}$ in combination with one or more other trivalent lanthanide metal ions.

In a seventh set of embodiments, the catalyst includes at least one trivalent transition metal ion and at least one trivalent lanthanide metal ion. For example, in particular embodiments, at least one trivalent metal ion is selected from $Sc^{+3}$, $Fe^{+3}$, $V^{+3}$, $Cr^{+3}$, and/or $Y^{+3}$ and another trivalent metal ion is selected from $La^{+3}$, $Ce^{+3}$, $Pr^{+3}$, and/or $Nd^{+3}$.

In an eighth set of embodiments, the catalyst includes at least one trivalent transition metal ion and at least one trivalent main group metal ion. For example, in particular embodiments, at least one trivalent metal ion is selected from $Sc^{+3}$, $Fe^{+3}$, $V^{+3}$, $Cr^{+3}$, and/or $Y^{+3}$ and another trivalent metal ion is selected from $In^{+3}$, $Ga^{+3}$, $As^{+3}$, $Sb^{+3}$, and/or $Bi^{+3}$.

In a ninth set of embodiments, the catalyst includes at least one trivalent main group metal ion and at least one trivalent lanthanide metal ion. For example, in particular embodiments, at least one trivalent metal ion is selected from $In^{+3}$, $Ga^{+3}$, $As^{+3}$, $Sb^{+3}$, and/or $Bi^{+3}$, and another trivalent metal ion is selected from $La^{+3}$, $Ce^{+3}$, $Pr^{+3}$, and/or $Nd^{+3}$.

In a tenth set of embodiments, the catalyst includes at least three trivalent metal ions. The at least three trivalent metal ions can be selected from trivalent transition metal ions, trivalent main group metal ions, and/or trivalent lanthanide metal ions. For example, the catalyst may include at least two metal ions selected from $Sc^{+3}$, $Fe^{+3}$, $V^{+3}$, $Cr^{+3}$, $Y^{+3}$, $In^{+3}$, $Ga^{+3}$, $As^{+3}$, $Sb^{+3}$, and/or $Bi^{+3}$, and an additional metal ion selected from any of the foregoing metal ions and different from the first two metal ions.

In particular embodiments, one, two, three, or more trivalent metal ions are selected from $Sc^{+3}$, $Fe^{+3}$, $V^{+3}$, $Y^{+3}$, $La^{+3}$, $Ce^{+3}$, $Pr^{+3}$, $Nd^{+3}$, $In^{+3}$, and/or $Ga^{+3}$. In more particular embodiments, one, two, three, or more trivalent metal ions are selected from $Sc^{+3}$, $Fe^{+3}$, $V^{+3}$, $La^{+3}$, $Ga^{+3}$, and/or $In^{+3}$.

The zeolite catalyst described above is typically not coated with a metal-containing film or layer. However, the instant invention also contemplates the zeolite catalyst described above coated with a metal-containing film or layer as long as the film or layer does not substantially impede the catalyst from effectively functioning as a conversion catalyst, as intended herein. By being coated, the film or layer resides on the surface of the zeolite. In some embodiments, the surface of the zeolite refers to only the outer surface (i.e., as defined by the outer contour area of the zeolite catalyst), while in other embodiments, the surface of the zeolite refers to or includes inner surfaces of the zeolite, such as the surfaces within pores or channels of the zeolite. The metal-containing film or layer can serve, for example, to adjust the physical characteristics of the catalyst, the catalytic efficiency, or catalytic selectivity. Some examples of metal-containing surfaces include the oxides and/or sulfides of the alkali metals, alkaline earth metals, and divalent transition or main group metals, provided that such surface metals are non-contaminating to the hydrocarbon product and non-deleterious to the conversion process.

The catalyst described herein can be synthesized by any of the methods well known in the art, such as the acidic ion exchange method, as described in, for example, N. A. S. Amin et al., *Journal of Natural Gas Chemistry*, 12 (2003), pp. 123-134. The method considered herein should preferably incorporate the metal ions homogeneously into the zeolite. The zeolite may be a single type of zeolite, or a combination of different zeolite materials.

In particular embodiments, the catalyst described herein is prepared by, first, impregnating the zeolite with the metals to be loaded. The impregnating step can be achieved by, for example, treating the zeolite with one or more solutions containing salts of the metals to be loaded. By treating the zeolite with the metal-containing solution, the metal-containing solution is contacted with the zeolite such that the solution is absorbed into the zeolite, preferably into the entire volume of the zeolite. Typically, in preparing the metal-loaded zeolite catalyst (e.g., V-ZSM-5, Ga-ZSM-5, In-ZSM-5, Cu-ZSM5, Fe-ZSM-5, Sc-ZSM-5, Ti-ZSM-5, Cr-ZSM-5, Zn-ZSM-5, or Cd-ZSM-5), the acid zeolite form (i.e., H-ZSM5) or its ammonium salt (e.g., $NH_4$-ZSM-5) is used as a starting material on which an exchange with metal ions (e.g., copper ions) is performed. The particulars of such metal exchange processes are well known in the art, as indicated above.

In one embodiment, the impregnating step is achieved by treating the zeolite with a solution that contains all of the metals to be loaded. In another embodiment, the impregnating step is achieved by treating the zeolite with two or more solutions, wherein the different solutions contain different metals or combinations of metals. Each treatment of the zeolite with an impregnating solution corresponds to a separate impregnating step. Typically, when more than one impregnating step is employed, a drying and/or thermal treatment step is employed between the impregnating steps.

The metal-impregnating solution contains at least one or more metal ions to be loaded into the zeolite, as well as a liquid carrier for distributing the metal ions into the zeolite. The metal ions are generally in the form of metal salts. Preferably, the metal salts are completely dissolved in the liquid carrier. The metal salt contains one or more metal ions in ionic association with one or more counteranions. Any one or more of the metal ions described above can serve as the metal ion portion. The counteranion can be selected from, for example, halides ($F^-$, $Cl^-$, $Br^-$, or $I^-$), carboxylates (e.g., formate, acetate, propionate, or butyrate), sulfate, nitrate, phosphate, chlorate, bromate, iodate, hydroxide, β-diketonate (e.g., acetylacetonate), and dicarboxylates (e.g., oxalate, malonate, or succinate).

In particular embodiments, the catalyst is prepared by forming a slurry containing zeolite powder and the metals to be incorporated. The resulting slurry is dried and fired to form a powder. The powder is then combined with organic and/or inorganic binders and wet-mixed to form a paste. The resulting paste can be formed into any desired shape, e.g., by extrusion into rod, honeycomb, or pinwheel structures. The extruded structures are then dried and fired to form the final catalyst. In other embodiments, the zeolite powder, metals, and binders are all combined together to form a paste, which is then extruded and fired.

After impregnating the zeolite, the metal-loaded zeolite is typically dried and/or subjected to a thermal treatment step (e.g., a firing or calcination step). The thermal treatment step functions to permanently incorporate the impregnated metals into the zeolite, e.g., by replacing $Al^{+3}$ and/or $Si^{+4}$ and forming metal-oxide bonds within the zeolite material. In different embodiments, the thermal treatment step can be conducted at a temperature of at least 100° C., 150° C., 200° C., 250° C., 300° C., 350° C., 400° C., 450° C., 500° C., 550° C., 600° C., 650° C., 700° C., 750° C., or 800° C., or within a range therein, for a time period of, for example, 15 minutes, 30 minutes, 1 hour, 2 hours, 6 hours, 12 hours, 24 hours, 30 hours, 36 hours, or 48 hours, or within a range therein. In some particular embodiments, the thermal treatment step is conducted at a temperature of at least 500° C. for a time period of at least two hours. In some embodiments, the thermal treatment step includes a temperature ramping step from a lower temperature to a higher temperature, and/or from a higher temperature to a lower temperature. For example, the thermal treatment step can include a ramp stage from 100-700° C., or vice-versa, at a rate of 1, 2, 5, or 10° C./min.

Generally, the one or more heat treatment steps for producing the metal-loaded zeolite catalyst are conducted under normal atmospheric pressure. However, in some embodiments, an elevated pressure (e.g., above 1 atm and up to 2, 5, or 10 atm) is employed, while in other embodiments, a reduced pressure (e.g., below 1, 0.5, or 0.2 atm) is employed. Furthermore, although the heat treatment steps are generally conducted under a normal air atmosphere, in some embodiments, an elevated oxygen, reduced oxygen, or inert atmosphere is used. Some gases that can be included in the processing atmosphere include, for example, oxygen, nitrogen, helium, argon, carbon dioxide, and mixtures thereof.

As a more descriptive example, a V-ZSM-5 catalyst can be prepared as follows: a 0.050 M solution of $V(III)Cl_3$ is first made by dissolving 2.5 g of $V(III)Cl_3$ into 320 mL of distilled water. Then, 12.17 g of $NH_4^+$-ZSM-5 is added to the aqueous solution and warmed to about 80° C. After stirring for eight hours, the heterogeneous mixture is vacuum filtered, and the filtrate discarded. The light blue V-ZSM-5 initial solid product is then calcined at 500° C. for four hours, to produce a light yellow solid product. A Ga-ZSM-5 catalyst can be produced analogously, along with stoichiometric adjustments, by using a gallium salt, such as a gallium nitrate salt, in place of the vanadium chloride.

Similarly, a Cu-ZSM-5 catalyst can be prepared as follows: 2.664 g of copper acetate hydrate (i.e., $Cu(OAc)_2 \cdot 6H_2O$) is dissolved in 600 mL de-ionized water (0.015M), followed by addition of 10.005 g of H-ZSM-5 zeolite. The slurry is kept stirring for about two hours at 50° C. Cu-ZSM-5 (blue in color) is collected by filtration after cooling, washed with de-ionized water, and calcined in air at about 500° C. (10° C./min) for four hours.

The produced metal-loaded zeolite can then be further impregnated with another metal. For example, Cu—Fe-ZSM-5 can be produced as follows: 5 g of Cu-ZSM-5 is suspended in an aqueous solution of 25 mL of 0.015M $Fe(NO_3)_3$, degassed with $N_2$, and is kept stirring for about two hours at about 80° C. Brown solid is obtained after filtration, leaving a clear and colorless filtrate. The product is then calcined in air at about 500° C. (2° C./min) for about two hours. The resulting Cu—Fe-ZSM-5 catalyst typically contains about 2.4% Cu and 0.3% Fe. Numerous other metals can be loaded into the zeolite by similar means to produce a variety of different metal-loaded catalysts, such as a Cu—V-ZSM-5, Fe—V-ZSM-5, Cu—Fe—V-ZSM-5, Ga—V-ZSM-5, In—V-ZSM-5, Ga—Cu-ZSM-5, Ga—Fe-ZSM-5, Ga—Cu—Fe-ZSM-5, In—Cu-ZSM-5, In—Fe-ZSM-5, or In—Cu—Fe-ZSM-5 catalyst.

Generally, the zeolite catalyst described herein is in the form of a powder. In a first set of embodiments, at least a portion, or all, of the particles of the powder have a size less than a micron (i.e., nanosized particles). The nanosized particles can have a particle size of precisely, at least, up to, or less than, for example, 1, 2, 5, 10, 20, 30, 40, 50, 60, 70, 80, 90, 100, 150, 200, 250, 300, 350, 400, 450, 500, 550, 600, 650, 700, 750, 800, 850, 900, or 950 nanometers (nm), or a particle size within a range bounded by any two of the foregoing values. In a second set of embodiments, at least a portion, or all, of the particles of the powder have a size at or above 1 micron in size. The micron-sized particles can have a particle size of precisely, at least, up to, or less than, for example, 1, 2, 5, 10, 20, 30, 40, 50, 60, 70, 80, 90, or 100 microns (m), or a particle size within a range bounded by any two of the foregoing values. In some embodiments, single crystals or grains of the catalyst correspond to any of the sizes provided above, while in other embodiments, crystals or grains of the catalyst are agglomerated to provide agglomerated crystallites or grains having any of the above exemplary dimensions.

In other embodiments, the zeolite catalyst can be in the form of a film, a coating, or a multiplicity of films or coatings. The thickness of the coatings or multiplicity of coatings can be, for example, 1, 2, 5, 10, 50, or 100 microns, or a range therein, or up to 100 micron thickness. In yet other embodiments, the zeolite catalyst is in the form of a non-particulate (i.e., continuous) bulk solid. In still other embodiments, the zeolite catalyst can be fibrous or in the form of a mesh. In yet another embodiment, the zeolite catalyst can be extruded into various shapes, such as honeycombs, small cylinders, or small tubes.

The catalyst can also be mixed with or affixed onto a support material. The support material can be a powder (e.g., having any of the above particle sizes), granular (e.g., 0.5 mm or greater particle size), a bulk material, such as a honeycomb monolith of the flow-through type, a plate or multi-plate structure, or corrugated metal sheets. If a honeycomb structure is used, the honeycomb structure can contain any suitable density of cells. For example, the honeycomb structure can have 100, 200, 300, 400, 500, 600, 700, 800, or 900 cells per square inch (cells/in$^2$) (or from 62-140 cells/cm$^2$) or greater. The support material is generally constructed of a refractory composition, such as those containing cordierite, mullite, alumina (e.g., α-, β-, or γ-alumina), or zirconia, or a combination thereof. Honeycomb structures, in particular, are described in detail in, for example, U.S. Pat. Nos. 5,314,665, 7,442,425, and 7,438,868, the contents of which are incorporated herein by reference in their entirety. When corrugated or other types of metal sheets are used, these can be layered on top of each other with catalyst material supported on the sheets such that passages remain that allow the flow of alcohol-containing fluid. The layered sheets can also be formed into a structure, such as a cylinder, by winding the sheets.

The method described in this disclosure improves on the conventional alcohol-to-hydrocarbon conversion processes of the art by diminishing the gaseous hydrocarbon fraction and maximizing the liquid gaseous hydrocarbon fraction. The method achieves this by, in a first step (i.e., step i), producing a first hydrocarbon fraction from one or more alcohols by contacting the one or more alcohols with a metal-loaded zeolite catalyst, wherein the first hydrocarbon fraction has any of the liquid and gaseous hydrocarbon compositions and distributions described above, and which may or may not overlap with typical compositions and relative concentrations encountered in the conventional art. In a second step (i.e., step ii), either after or during production of the first hydrocarbon fraction, the method selectively removes at least a portion of gaseous hydrocarbons having less than five carbon atoms from the first hydrocarbon fraction, as described above, having both liquid and gaseous hydrocarbon portions (i.e., liquid and gaseous hydrocarbon fractions or sub-fractions). At least a portion of the gaseous hydrocarbons, as removed, are then contacted with a metal-loaded zeolite, as described above, under conditions suitable for converting at least a portion of the gaseous hydrocarbons into liquid hydrocarbons having at least five carbon atoms. The original and additional liquid hydrocarbons along with any remaining or newly produced gaseous hydrocarbons produced in steps (i) and (ii) altogether result in a second (i.e., combined) hydrocarbon fraction reduced in gaseous hydrocarbon content and enriched in liquid hydrocarbon content. The second hydrocarbon fraction reduced in gaseous hydrocarbon content may also, in turn, have gaseous hydrocarbons selectively removed therefrom, and the gaseous hydrocarbons processed again to enrich the level of liquid hydrocarbons. The process may be repeated any number of times to produce a subsequent hydrocarbon fraction reduced in gaseous hydrocarbons, or the process may be conducted on a continuous basis without discrete steps in the selective removal and re-processing of the gaseous hydrocarbons. The metal-loaded zeolite that produces the first hydrocarbon fraction and the metal-loaded zeolite that further processes the gaseous hydrocarbons are independently any of the metal-loaded zeolites described above, and may be the same or different in composition or location.

In some embodiments, the process is practiced as a single-zone (or recirculation) process. In the single-zone process, gaseous hydrocarbons in step (ii) are recirculated back to the metal-loaded zeolite catalyst used in step (i) while the metal-loaded zeolite catalyst used in step (i) continues to convert the alcohol to the first hydrocarbon fraction. Thus, by the single-zone process, recirculated gaseous hydrocarbon species are converted into higher liquid hydrocarbon species simultaneous with continued production of liquid and additional gaseous hydrocarbon species, the latter of which are again and continuously recirculated back to the zone in which alcohol-to-hydrocarbon conversion continues to occur. Generally, the alcohol being converted in step (i) continues to be fed into the conversion zone as gaseous hydrocarbons are selectively removed and recirculated back into the conversion zone. However, if desired, the single-zone process may be practiced by cessation of the alcohol feed before, during, or after recirculation of the gaseous hydrocarbons into the conversion zone. In some embodiments, the alcohol may be fed intermittently or as desired during recirculation of the gaseous hydrocarbons into the conversion zone. In particular embodiments, the metal-loaded zeolite catalyst used in the single-zone process is selected from V-ZSM-5, Ga-ZSM-5, In-ZSM-5, Cu-ZSM5, Fe-ZSM-5, Sc-ZSM-5, Ti-ZSM-5, Cr-ZSM-5, Zn-ZSM-5, or Cd-ZSM-5, or a mixture thereof, or a catalyst containing a combination of any two or three of the foregoing metals in heterobimetallic form.

In other embodiments, the process is practiced as a two-zone process. In the two-zone process, step (i) is conducted in a first zone containing a first metal-loaded zeolite catalyst, and the gaseous hydrocarbons selectively removed in step (ii) are transported from the first zone to a second zone in which the gaseous hydrocarbons are contacted with a second metal-loaded zeolite catalyst under conditions suitable for converting the gaseous hydrocarbons into liquid hydrocarbons having at least five carbon atoms. The metal-loaded zeolite catalyst that produces the first hydrocarbon fraction in the first zone and the metal-loaded zeolite catalyst that further processes the gaseous hydrocarbons in the second zone are independently any of the metal-loaded zeolites described above, and may be the same or different in composition. In particular embodiments, the metal-loaded zeolite catalysts used in the two-zone process are independently selected from V-ZSM-5, Ga-ZSM-5, In-ZSM-5, Cu-ZSM5, Fe-ZSM-5, Sc-ZSM-5, Ti-ZSM-5, Cr-ZSM-5, Zn-ZSM-5, or Cd-ZSM-5, or a mixture thereof, or a catalyst containing a combination of any two or three of the foregoing metals in heterobimetallic form. Notably, the two-zone process provides the advantage of permitting very different conditions (e.g., in temperature and/or pressure) in the first and second zones. Hence, as the two zones perform different functions, each zone can be independently optimized in its conditions to maximize its purpose. For example, while the first zone, whose purpose is to convert alcohols to hydrocarbons, may be operated at any of the conditions described above (e.g., temperature of 100 to 550° C.), the second zone, whose purpose is to convert gaseous hydrocarbons to liquid hydrocarbons, may be operated at significantly higher temperatures (e.g., at least or above 600, 650, 700, 750, or 800° C.) and possibly elevated pressures, which may be unsuitable for the first zone. In some embodiments, the two zones are operated within a temperature range of 100 to 550° C., or within the same or different sub-range therein. For example, the first zone may be operated at a temperature of 200-450° C., while the second zone may be operated at a temperature of above 450° C. or at least or above 475° C., 500° C., 510° C., 520° C., 550° C., or 600° C., or within a range bounded by any two of the foregoing values.

The above-described method results in a hydrocarbon fraction reduced in gaseous hydrocarbon content. The hydrocarbon fraction reduced in gaseous hydrocarbon content typically contains total liquid hydrocarbon compounds (i.e., the liquid hydrocarbon fraction) in an amount of at least or above 50% per total hydrocarbon fraction. Conversely, the hydrocarbon fraction reduced in gaseous hydrocarbon content typically contains total gaseous hydrocarbon compounds (i.e., the gaseous hydrocarbon fraction) in an amount of up to or less than 50% per total hydrocarbon fraction (i.e., per total of all hydrocarbons produced). In different embodiments, the liquid hydrocarbon fraction is in an amount of at least or above, for example, 55%, 60%, 65%, 70%, 75%, 80%, 85%, 90%, 92%, or 95% per total hydrocarbon fraction. Conversely, in different embodiments, the gaseous hydrocarbon fraction is in an amount of up to or less than, for example, 45%, 40%, 35%, 30%, 25%, 20%, 15%, 10%, 8%, or 5% per total hydrocarbon fraction.

In some embodiments, the conversion method described above is integrated with a fermentation process, wherein the fermentation process produces the alcohol used as feedstock for the conversion process. By being "integrated" is meant that alcohol produced at a fermentation facility or zone is sent to and processed at a conversion facility or zone (which performs the conversion process described above). Preferably, in order to minimize production costs, the fermentation process is in close enough proximity to the conversion facility or zone, or includes appropriate conduits for transferring produced alcohol to the conversion facility or zone, thereby not requiring the alcohol to be shipped. In particular embodiments, the fermentation stream produced in the fermentation facility is directly transferred to the conversion facility, generally with removal of solids from the raw stream (generally by filtration or settling) before contact of the stream with the catalyst.

In some embodiments, the fermentation process is performed in an autonomous fermentation facility, i.e., where saccharides, produced elsewhere, are loaded into the fermentation facility to produce alcohol. In other embodiments, the fermentation process is part of a larger biomass reactor facility, i.e., where biomass is decomposed into fermentable saccharides, which are then processed in a fermentation zone. Biomass reactors and fermentation facilities are well known in the art. Biomass often refers to lignocellulosic matter (i.e., plant material), such as wood, grass, leaves, paper, corn husks, sugar cane, bagasse, and nut hulls. Generally, biomass-to-ethanol conversion is performed by 1) pretreating biomass under well-known conditions to loosen lignin and hemicellulosic material from cellulosic material, 2) breaking down cellulosic material into fermentable saccharide material by the action of a cellulase enzyme, and 3) fermentation of the saccharide material, typically by the action of a fermenting organism, such as suitable yeast, to produce one or more alcohols.

In other embodiments, the alcohol is produced from a more direct sugar source, such as a plant-based source of sugars, such as sugar cane or a grain starch (such as corn starch). Ethanol production via corn starch (i.e., corn starch ethanol) and via sugar cane (i.e., cane sugar ethanol) currently represent some of the largest commercial production methods of ethanol. Integration of the instant conversion process with any of these large scale ethanol production methods is contemplated herein.

Examples have been set forth below for the purpose of illustration and to describe certain specific embodiments of the invention. However, the scope of this invention is not to be in any way limited by the examples set forth herein.

Examples

Two-Step Process

An olefin mixture (6% of ethylene, 3% of propene, 3% of propane, 0.1% of isobutane, 1.04% of isobutylene and 2% of cis-2-butene) was used to simulate the light (gaseous) products ($C_2$-$C_4$) from ethanol conversion. Ethanol was converted to hydrocarbons and water over metal-exchanged ZSM-5 catalyst loaded with, for example, V, Ga, or Cr. The water was removed, the liquid fraction was collected, and gaseous hydrocarbons ($C_2$-$C_4$) were fed to a second zone of the catalyst reactor containing a ZSM-5 catalyst independently loaded with any of the same metals. A 20 ccm flow of the olefin mixture was fed into the reactor using 200 mg catalyst, wherein "ccm" refers to "cubic centimeter per minute".

For V-ZSM-5, 94% of ethylene, 87% of propene, 79% of isobutylene and 98% of 2-butene were converted at 350° C. to liquid products. The total carbon conversion to liquid products was 33%. Increasing the temperature from 350° C. to 500° C. did not improve the yield.

For Ga-ZSM-5, 96% of ethylene, 94% of propene, 69% of isobutene, 98% of isobutylene and 100% of 2-butene were converted at 450° C. to liquid products. The total carbon conversion to liquid products was 70%. Increasing the temperature from 350° C. to 500° C. led to an increase in liquid products from 41% to 72%.

Simulated One-Step (Recirculation) Process—Light Gas Co-Feeding with Ethanol on V-ZSM-5 Catalyst Light gases ($C_2$-$C_4$) are produced during ethanol conversion on ZSM-5, including ethylene, ethane, propene, propane, isobutane, 2-butene, butane and isobutylene. To increase the liquid hydrocarbon production ($C_5^+$) from ethanol conversion, these light gases can be co-fed with ethanol. The following experiments investigated the effect of the co-feeding on liquid hydrocarbon yield, liquid composition, and the reactivities of these light gases under co-feeding conditions. This study employed a simulated light gas mixture to co-feed with ethanol on V-ZSM-5. The composition of the simulated light gas mixture is: 6% ethylene, 3% propene, 3% propane, 1000 ppm isobutane, 2% cis-2-butene, 1.04% isobutylene and balance nitrogen. The catalyst, V-ZSM-5, was prepared by the conventional ion exchange method, and 0.2 g of this catalyst was used. The ethanol liquid flow rate was 0.4 mL/h. All of the reactions were conducted in a continuous fixed bed reactor under ambient pressure. All liquid yields are based on ethanol when pure ethanol or ethanol-lights mixture are in input stream. For lights only in input stream without ethanol, the yield is conversion of lights to $C_5^+$ hydrocarbons.

Temperature Effect:

When only ethanol was used as the reactant, 359° C. (~350° C. inlet gas temperature) was found to be the optimum catalyst temperature for maximum liquid hydrocarbon production (~33%). When 10 ccm of simulated light gas mixture was co-fed with ethanol, liquid yields at various temperatures were investigated. The maximum liquid yield (51%) was still achieved at ~359° C. (catalyst temperature).

FIG. 1 is a graph plotting liquid hydrocarbon yield ($C_5^+$) at different catalyst temperatures with 0.2 g V-ZSM-5 and 0.4 mL/h ethanol feed, and either co-feeding with 10 ccm of the light gas mixture, or no co-feeding of a light gas mixture. As shown in FIG. 1, the liquid hydrocarbon yield was maximized at a temperature of ~359° C. (i.e., ~51%) and at temperatures of about 300° C., 400° C., and 450° C., the liquid hydrocarbon yields were all around 40%, which are higher than those with only ethanol feed.

Liquid Hydrocarbon Yield at Different Light Gas Co-Feeding:

Since 359° C. was the optimum catalyst temperature for light gas co-feeding, the following experiment investigated the effect of co-feeding flow rate on liquid hydrocarbon yield and ethanol conversion at this temperature. For each experiment, there was only ethanol flow for the first two hours and the light gas mixture was co-fed after that.

Figure 2:
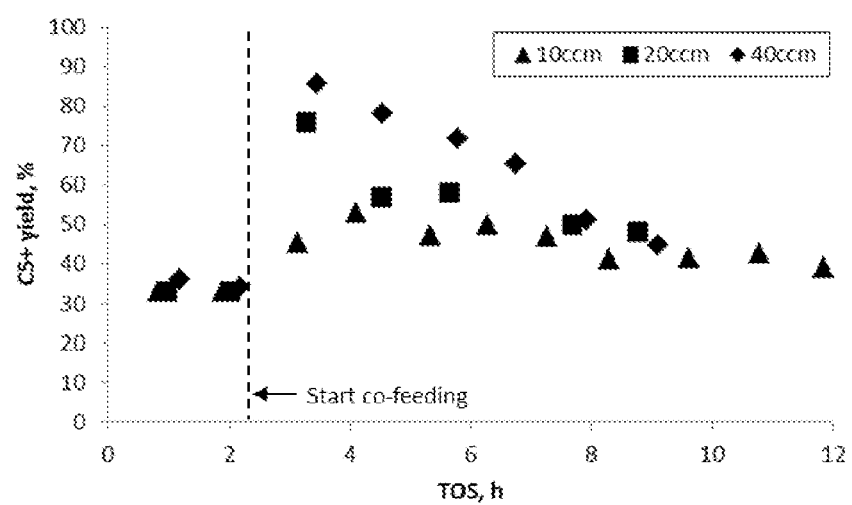
FIG. 2. Graph plotting liquid yields vs. time on stream (TOS) in hours at 10 ccm, 20 ccm, and 40 ccm light gas co-feeding with 0.2 g V-ZSM-5 catalyst and 0.4 mL/h ethanol flow at 359° C. catalyst temperature.

FIG. 2 is a graph plotting liquid yields vs. time on stream (TOS) in hours for 10 ccm, 20 ccm, and 40 ccm light gas co-feeding with 0.2 g V-ZSM-5 catalyst and 0.4 mL/h ethanol flow at 359° C. catalyst temperature. As shown in FIG. 2, at 359° C., ~33% liquid yield was achieved with only ethanol feed (left of the dotted vertical line). When 10 ccm of simulated light gas mixture was co-fed (right of the dotted vertical line), the liquid yield increased to ~53% at about 4 hours, and then gradually decreased to ~40% at about 12 hours. When 20 ccm of simulated light gas mixture was co-fed, the liquid yield maximized at ~76% at about 3 hours and decreased to ~50% at about 9 hours. As expected, the catalyst deactivated faster when co-feeding increased. When 40 ccm of simulated light gas mixture was co-fed, the liquid yield maximized at ~86% at about 3.25 hours and dropped to about 45% after about 9 hours time on stream.

Figure 3:
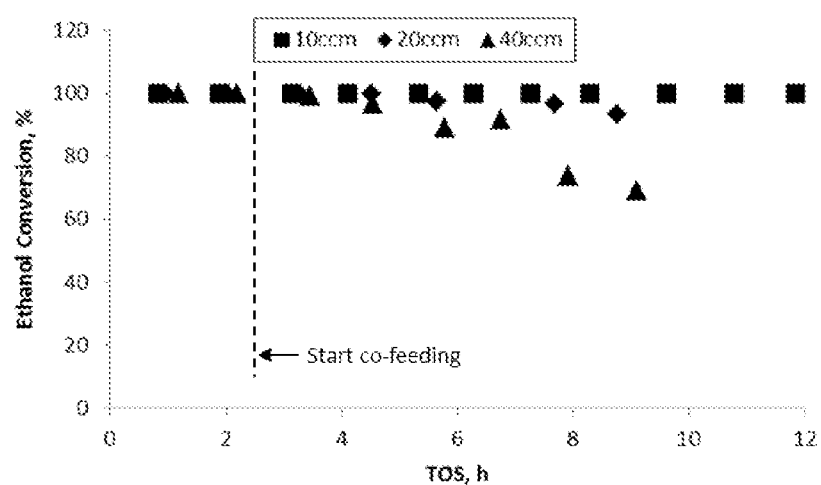
FIG. 3. Graph plotting ethanol conversion (%) vs. time on stream (TOS) in hours at 10 ccm, 20 ccm, and 40 ccm light gas co-feeding with 0.2 g V-ZSM-5 catalyst and 0.4 mL/h ethanol flow at 359° C. catalyst temperature.

Ethanol Conversion with Different Light Gas Co-Feeding:

FIG. 3 is a graph plotting ethanol conversion (%) vs. time on stream (TOS) in hours for 10 ccm, 20 ccm, and 40 ccm light gas co-feeding with 0.2 g V-ZSM-5 catalyst and 0.4 mL/h ethanol flow at 359° C. catalyst temperature. As shown in FIG. 3, ethanol conversion was complete (100%) with only ethanol feed at a temperature of 359° C. When 10 ccm of light gas was co-fed, the ethanol conversion remained complete for 12 hours time on stream. Ethanol conversion dropped to 94% at 9 hours when 20 ccm of light gas was used. For 40 ccm light gas co-feeding, ethanol conversion decreased to 69% around 9 hours.

Figure 4A:
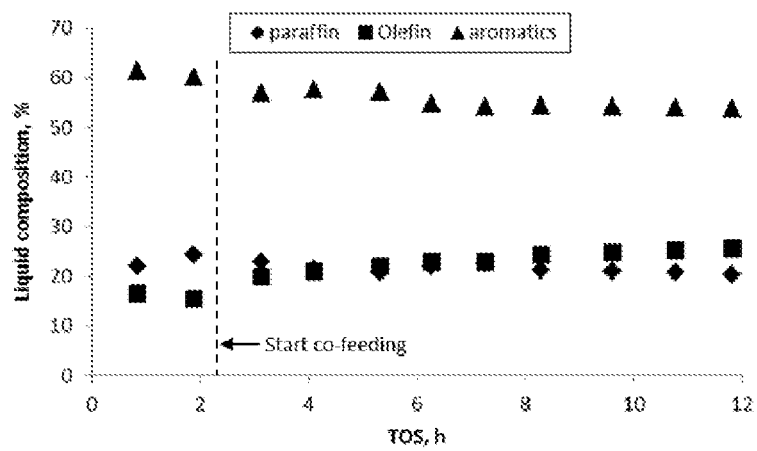
FIGS. 4A-4C.
Figure 4B:
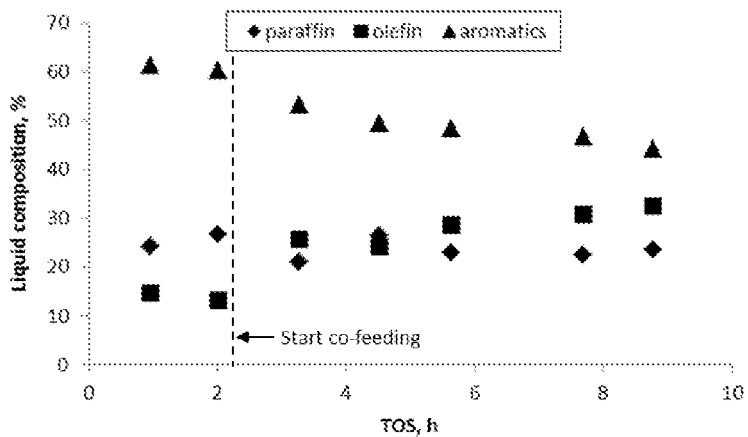
Figure 4C:
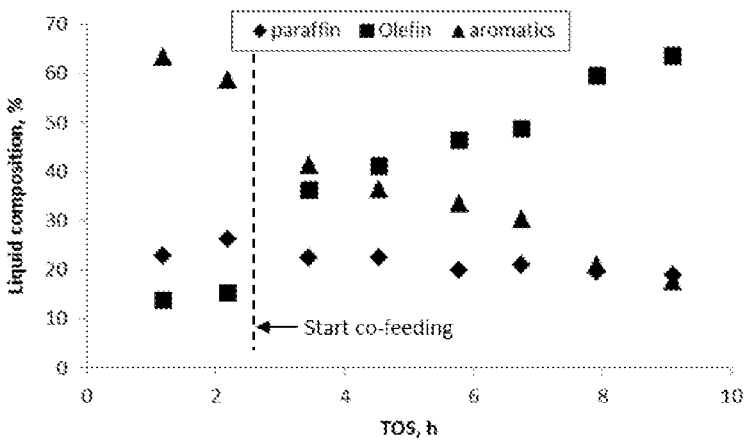

Liquid Hydrocarbon ($C_5^+$) Composition Changes with Different Light Gas Co-Feeding:

FIGS. 4A, 4B, and 4C are graphs plotting liquid composition (%) vs. time on stream (TOS) in hours for 10 ccm, 20 ccm, and 40 ccm, respectively, of light gas co-feeding using 0.2 g V-ZSM-5 catalyst and 0.4 mL/h ethanol flow at 359° C. catalyst temperature. Each plot shows the contributions of paraffins, olefins, and aromatics in the liquid compositions. As shown in FIGS. 4A-4C, when only ethanol was fed onto V-ZSM-5, there were ~23% paraffin, ~15% olefin, and ~62% aromatics in the liquid hydrocarbon. As shown in FIG. 4A, for a 10 ccm light gas co-feeding, the paraffins slightly decreased to ~20% at ~12 hours, olefin increased to ~26% and aromatics decreased to ~54%. As shown in FIG. 4B, for a 20 ccm light gas co-feeding, the paraffins did not change much, olefin increased to ~32% and aromatics dropped significantly to ~44% at about 9 hours TOS. As shown in FIG. 4C, for a 40 ccm light gas co-feeding, the paraffin slightly changed to ~19%, while olefin dramatically increased to ~64% and aromatics dropped to ~18%.

Figure 5:
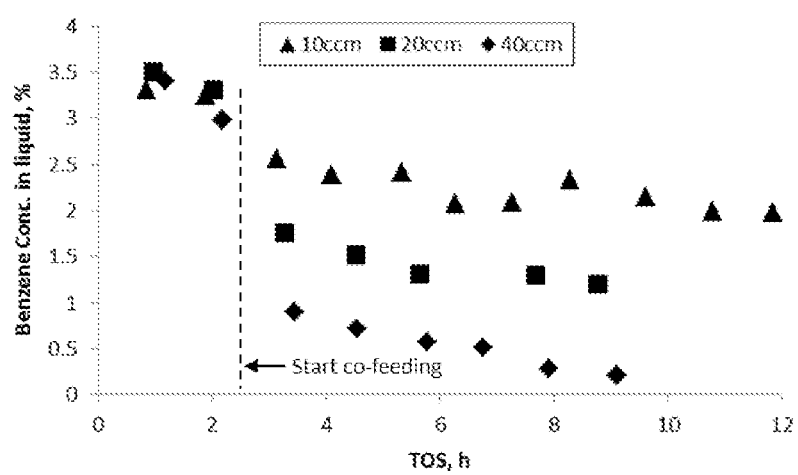
FIG. 5. Graph plotting benzene concentration in the liquid ($C_5^+$) hydrocarbon fraction at 10 ccm, 20 ccm, and 40 ccm light gas co-feeding with 0.2 g V-ZSM-5 catalyst and 0.4 mL/h ethanol flow at 359° C. catalyst temperature.

FIG. 5 is a graph plotting benzene concentration in the liquid ($C_5^+$) hydrocarbon fraction for 10 ccm, 20 ccm, and 40 ccm light gas co-feeding using 0.2 g V-ZSM-5 catalyst and 0.4 mL/h ethanol flow at 359° C. catalyst temperature. As shown in FIG. 5, when only ethanol was fed onto V-ZSM-5, benzene concentration in the final liquid hydrocarbon was 3.4%, much higher than the EPA requirement of 0.68%. Significantly, light gas co-feeding can greatly decrease benzene concentration. As shown in FIG. 5, higher light gas co-feeding resulted in much lower benzene concentration. For example, when a 40 ccm light gas mixture was co-fed, the benzene concentration was 0.9% at 3.5 hours, then continued to drop to 0.2%, far below the EPA requirement.

Light Gas Conversion:

Using V-ZSM-5 catalyst, during co-feeding, some of the light gases were converted to liquid hydrocarbons.

Figure 6A:
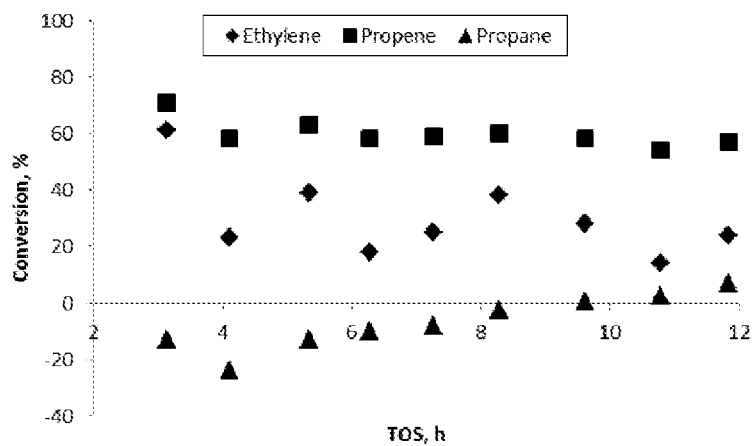
FIGS. 6A-6C.
Figure 6B:
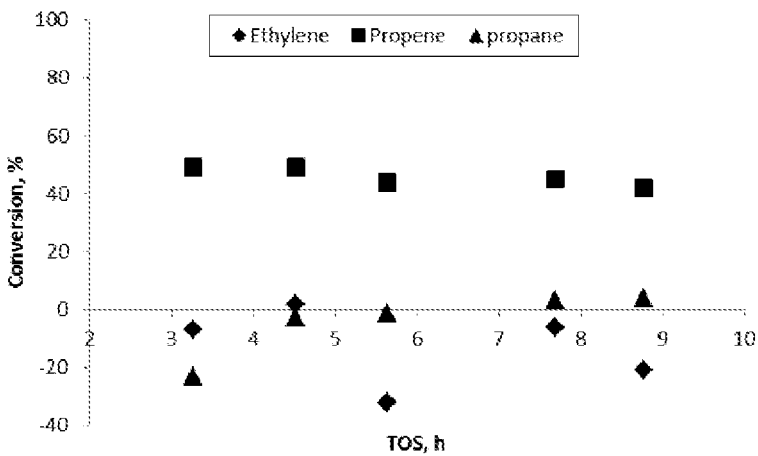
Figure 6C:
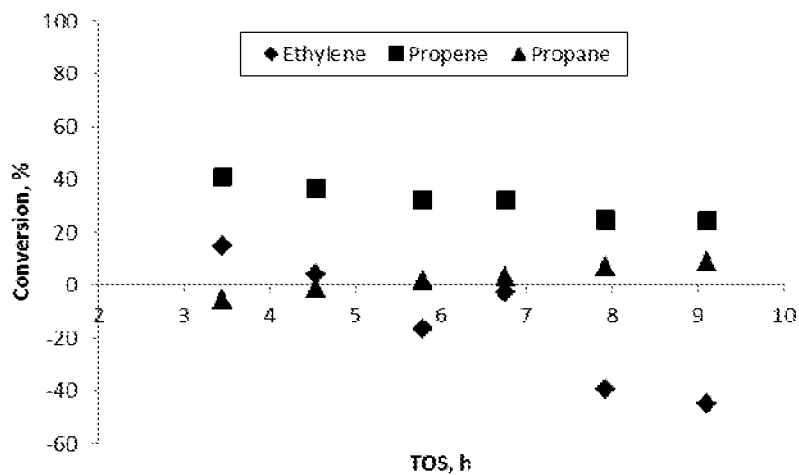

FIGS. 6A, 6B, and 6C are graphs plotting conversions (%) for ethylene, propene, and propane at 10 ccm (FIG. 6A), 20 ccm (FIG. 6B), and 40 ccm (FIG. 6C) light gas co-feeding using 0.2 g V-ZSM-5 catalyst and 0.4 mL/h ethanol flow at 359° C. catalyst temperature. A negative conversion indicates there was extra production of this gas. As shown in FIGS. 6A-6C, ethylene conversion fluctuated very largely, i.e., 14% to 61% for 10 ccm (FIG. 6A), −32% to 2% for 20 ccm (FIG. 6B), and −45% to 15% for 40 ccm (FIG. 6C) light gas co-feeding. Propene dropped from 71% to 57% for 10 ccm, 49% to 42% for 20 ccm, and 41% to 21% for 40 ccm light gas co-feeding. Propane changed from −24% to 7% for 10 ccm, −23% to 4% for 20 ccm, and −5% to 9% for 40 ccm light gas co-feeding.

Figure 7:
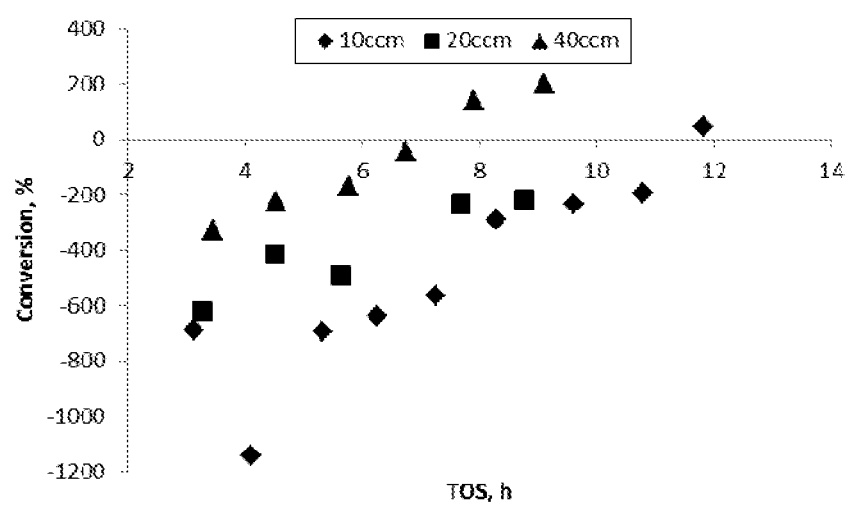
FIG. 7. Graph plotting conversions (%) for isobutane at 10 ccm, 20 ccm, and 40 ccm light gas co-feeding using 0.2 g V-ZSM-5 catalyst and 0.4 mL/h ethanol flow at 359° C. catalyst temperature.

FIG. 7 is a graph plotting conversions (%) for isobutane for 10 ccm, 20 ccm, and 40 ccm light gas co-feeding using 0.2 g V-ZSM-5 catalyst and 0.4 mL/h ethanol flow at 359° C. catalyst temperature. Isobutane concentration (1000 ppm) in the feed light gas was low. For this reason, we observed large numbers for both production and conversion. As shown in FIG. 7, for both 10 ccm and 20 ccm light gas co-feeding, extra isobutane was produced before 11 hours. For 40 ccm light gas flow, around 200% isobutane was converted after 7 hours, which means that not only isobutane in the feed light gas was converted, but also, isobutane directly produced from ethanol was also diminished.

Figure 8A:
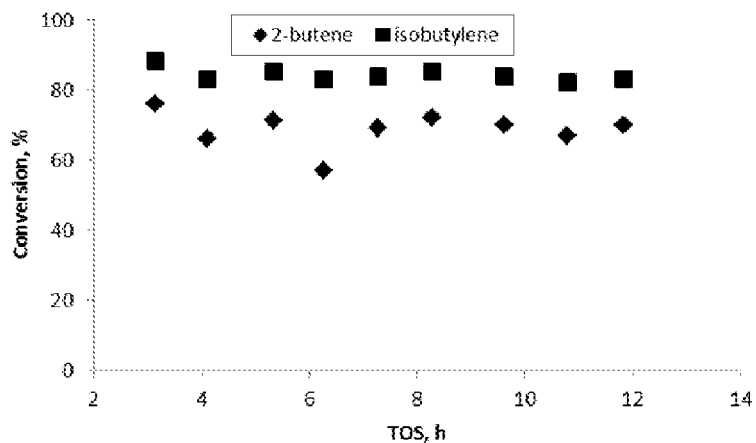
FIGS. 8A-8C.
Figure 8B:
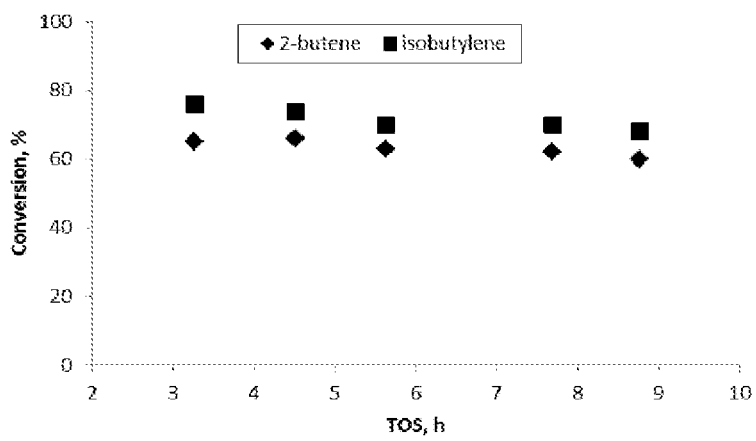
Figure 8C:
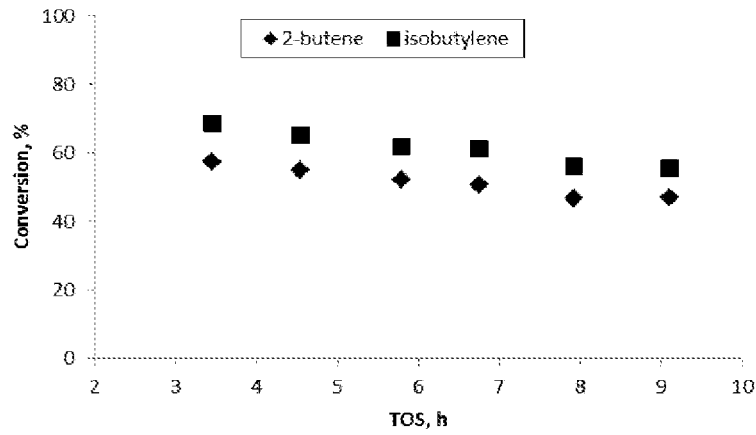

FIGS. 8A, 8B, and 8C are graphs plotting conversions (%) for isobutylene and 2-butene for 10 ccm (FIG. 8A), 20 ccm (FIG. 8B), and 40 ccm (FIG. 8C) light gas co-feeding using 0.2 g V-ZSM-5 catalyst and 0.4 mL/h ethanol flow at 359° C. catalyst temperature. As shown in FIGS. 8A-8C, both $C_4$ olefins (2-butene and isobutylene) were significantly converted to liquid hydrocarbons for each of the light gas flow rates. As expected, both 2-butene and isobutylene conversion slightly dropped as the light gas flow increased. For example, isobutylene conversion changed from 88% to 83% for the 10 ccm light gas co-feeding, and it decreased from 69% to 55% for the 40 ccm light gas co-feeding.

Only Feeding Simulated Light Gas Mixture on V-ZSM-5:

The simulated light gas mixture was also directly fed onto V-ZSM-5 without co-feeding with ethanol. The total gas flow was kept at 50 ccm while varying the light gas mixture flow.

Figure 9:
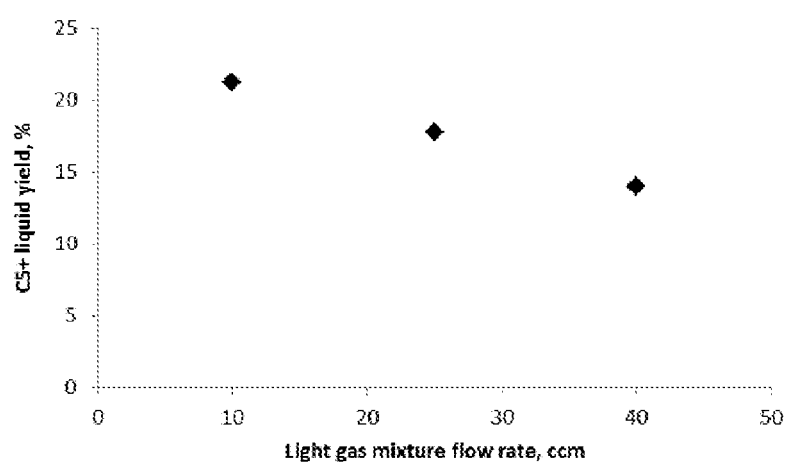
FIG. 9. Graph plotting liquid hydrocarbon ($C_5^+$) yield vs. light gas mixture flow rate (ccm) using 0.2 g V-ZSM-5 catalyst at 359° C. catalyst temperature and no ethanol co-feeding.

FIG. 9 is a graph plotting liquid hydrocarbon ($C_5^+$) yield vs. light gas mixture flow rate (ccm) using 0.2 g V-ZSM-5 catalyst at 359° C. catalyst temperature and no ethanol co-feeding. As shown in FIG. 9, liquid hydrocarbon yield decreased as the flow of light gas mixture increased. When the light gas mixture flow rate was 10 ccm, the liquid yield was about 21%, and the liquid yield dropped to about 14% at a light gas flow of 40 ccm.

Figure 10A:
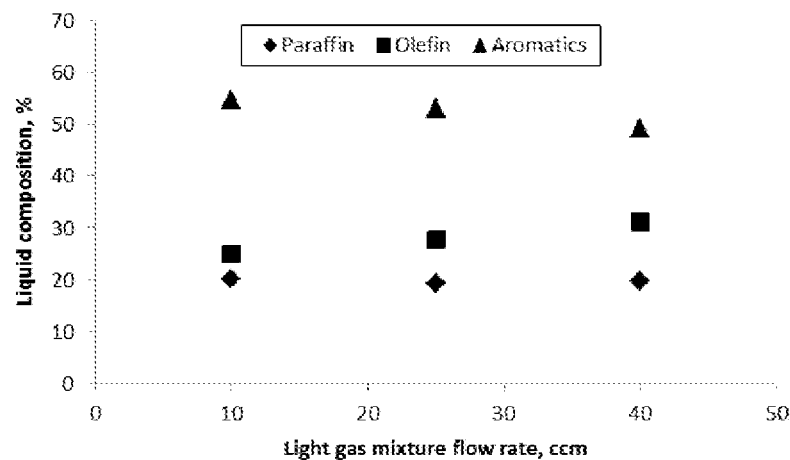
FIGS. 10A, 10B.
Figure 10B:
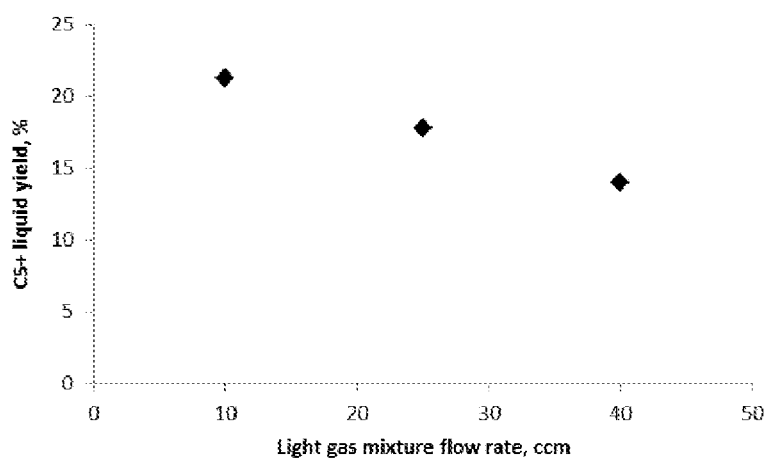

FIG. 10A is a graph plotting liquid composition in terms of relative amounts of paraffins, olefin, and aromatics vs. light gas mixture flow rate (ccm) using 0.2 g V-ZSM-5 catalyst at 359° C. catalyst temperature and no ethanol co-feeding. FIG. 10B is a graph plotting benzene concentration vs. light gas mixture flow rate (ccm) using 0.2 g V-ZSM-5 catalyst at 359° C. catalyst temperature and no ethanol co-feeding. As shown in FIG. 10A, when the light gas flow rate changed from 10 ccm to 40 ccm, aromatics decreased from 55% to 49%, olefin changed from 25% to 31%, and paraffin remained at 20%. As shown in FIG. 10B, when the light gas flow rate changed from 10 ccm to 40 ccm, benzene concentration lowered to 2.0% from 2.8%.

Figure 11A:
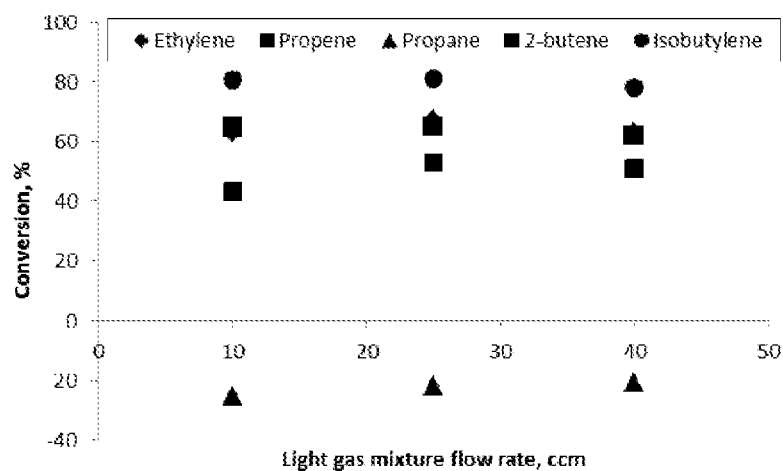
FIGS. 11A, 11B.
Figure 11B:
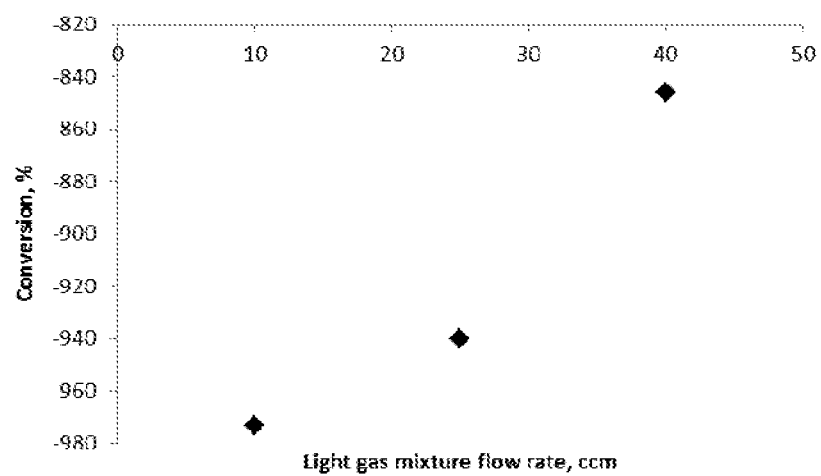

FIG. 11A is a graph plotting extent of conversion of ethylene, propene, propane, 2-butene, and isobutylene to liquid hydrocarbons (%) vs. light gas mixture flow rate (ccm) using 0.2 g V-ZSM-5 catalyst at 359° C. catalyst temperature and no ethanol co-feeding. FIG. 11B is a graph plotting extent of conversion of isobutane to liquid hydrocarbons (%) vs. light gas mixture flow rate (ccm) using 0.2 g V-ZSM-5 catalyst at 359° C. catalyst temperature and no ethanol co-feeding. As shown in FIGS. 11A and 11B, all of the olefins were converted significantly, with isobutylene at 78%-81%, 2-butene at 62%-65%, ethylene at 63%-67%, and propene at 43%-53%. Propane and isobutane were not converted, but 21%-26% propane was formed and 846%-973% of isobutane was produced, as only 1000 ppm isobutane was used as the reactant.

Simulated One-Step (Recirculation) Process—Light Gas Conversion on Ga-ZSM-5 Catalyst Olefins were shown, in the above results, to be converted to liquid hydrocarbons on V-ZSM-5 during co-feeding with ethanol. However, alkanes, such as propane and isobutane, showed difficulty in reacting on V-ZSM-5 at various temperatures from 350-550° C. However, as further shown in the results below, Ga-ZSM-5 has been observed to convert alkanes. To better understand the reactivities of the light gas on Ga-ZSM-5, the following experiment employed a simulated light gas mixture as a feed on Ga-ZSM-5, with the composition of the simulated light gas mixture being: 6% ethylene, 3% propene, 3% propane, 1000 ppm isobutane, 2% cis-2-butene, 1.04% isobutylene and balance nitrogen. The catalyst, Ga-ZSM-5, was prepared by the conventional ion exchange method, and 0.2 g of this catalyst was used. All the reactions were carried out in a continuous fixed bed reactor under ambient pressure.

Light gas mixture conversions on Ga-ZSM-5 (6.8% Ga loading) at various temperatures are shown in Table 1 below. At 450° C., all of the olefins showed significant conversions to liquid hydrocarbons, while the alkanes, propane and isobutane, did not react. Surprisingly, when the temperature was raised to 505° C., both alkanes showed large conversions, with propane at 49% and isobutane at 70%. Even at 478° C., slight conversions of propane and isobutane were observed. However, since the catalyst was on stream for 6.2 hours, significant deactivation could happen.

TABLE 1

Light gas mixture conversion with 0.2 g Ga-ZSM-5 (6.8% Ga loading), 10 ccm light gas mixture flow at various catalyst temperatures in one experiment

| | | Conversion, % | | | | | |
|---|---|---|---|---|---|---|---|
| TOS, h | Temperature ° C. | Ethylene | Propene | Propane | Isobutane | 2-butene | Isobutylene |
| 0.8 | 450 | 69 | 73 | −26 | −80 | 94 | 97 |
| 1.9 | 450 | 64 | 68 | −15 | −88 | 93 | 96 |
| 4.0 | 505 | 61 | 70 | 49 | 70 | 95 | 97 |
| 6.2 | 478 | 4.3 | 3.6 | 2.2 | 3.7 | 24 | 48 |

Since alkane conversion at around 500° C. was very effective, catalyst stability at this temperature was investigated. In the case of light gas recycling in the first step, light gas flow coming from the first step would be small. Thus, 5 ccm light gas mixture flow was tested.

Light gas mixture conversions on Ga-ZSM-5 at 500° C. are shown in Table 2 below. After 4 hours on stream, all $C_4$ species remained at very high conversions, above 95%. Ethylene conversion dropped to 52% and propene decreased to 73%. Propane still showed 42% conversion. In the scenario that light gas is recycled in the first step, most of the olefins will be converted in the first step and Ga-ZSM-5 will have a much better stability. In any case, the above results demonstrate that Ga-ZSM-5 is able to convert alkanes to liquid hydrocarbons at temperatures above 478° C.

TABLE 2

Light gas mixture conversion with 0.2 g Ga-ZSM-5 (6.8% Ga loading) 5 ccm light gas mixture flow at 500° C. catalyst temperature

| TOS, h | Conversion, % | | | | | |
|---|---|---|---|---|---|---|
| | Ethylene | Propene | Propane | Isobutane | 2-butene | Isobutylene |
| 0.4 | 86 | 94 | 91 | 100 | 100 | 100 |
| 1.9 | 75 | 87 | 81 | 90 | 100 | 100 |
| 4.0 | 52 | 73 | 42 | 96 | 99 | 99 |

While there have been shown and described what are at present considered the preferred embodiments of the invention, those skilled in the art may make various changes and modifications which remain within the scope of the invention defined by the appended claims.

What is claimed is:

1. A method for converting ethanol in aqueous solution to a hydrocarbon fraction reduced in gaseous hydrocarbon content, the method comprising:
   (i) contacting said ethanol, which is produced by a fermentation process and is present in a concentration of at least 20% in said aqueous solution, with a first metal-loaded zeolite catalyst, wherein the first metal-loaded zeolite catalyst is V-ZSM-5, at a temperature of 350-550° C. to convert said ethanol to a first hydrocarbon fraction containing liquid hydrocarbons having at least five carbon atoms along with gaseous hydrocarbons having less than five carbon atoms, wherein said first metal-loaded zeolite catalyst is catalytically active for converting said ethanol to said first hydrocarbon fraction; and
   (ii) selectively removing said gaseous hydrocarbons from the first hydrocarbon fraction and contacting said gaseous hydrocarbons with a second metal-loaded zeolite catalyst selected from V-ZSM-5 and Ga-ZSM-5 at a temperature of 350-550° C. to convert said gaseous hydrocarbons into liquid hydrocarbons having at least five carbon atoms to produce a second hydrocarbon fraction reduced in gaseous hydrocarbon content, wherein the first and second metal-loaded zeolite catalyst in steps (i) and (ii) are the same or different, and wherein said second hydrocarbon fraction contains less than 1% benzene.

2. The method of claim 1, wherein step (i) is conducted in a first zone containing said first metal-loaded zeolite catalyst, and said gaseous hydrocarbons in step (ii) are transported from said first zone to a second zone in which said gaseous hydrocarbons are contacted with said second metal-loaded zeolite catalyst under conditions suitable for converting said gaseous hydrocarbons into liquid hydrocarbons having at least five carbon atoms.

3. The method of claim 1, wherein said gaseous hydrocarbons in step (ii) are recirculated back to the first metal-loaded zeolite catalyst used in step (i) while said first metal-loaded zeolite catalyst continues to convert said alcohol to the first hydrocarbon fraction.

4. The method of claim 1, wherein said second hydrocarbon fraction reduced in gaseous hydrocarbon content comprises a mixture of liquid hydrocarbon compounds useful as a fuel or as a blendstock component of a fuel.

5. The method of claim 4, wherein said mixture of liquid hydrocarbon compounds substantially corresponds to a petrochemical fraction.

6. The method of claim 5, wherein said petrochemical fraction substantially corresponds to a fuel selected from gasoline, kerosene, diesel, and jet propellant.

7. The method of claim 1, wherein said second hydrocarbon fraction reduced in gaseous hydrocarbon content, as produced in step (ii), contains said liquid hydrocarbon compounds having at least five carbon atoms in an amount of at least 70% per total hydrocarbon fraction.

8. The method of claim 1, wherein said second hydrocarbon fraction reduced in gaseous hydrocarbon content, as produced in step (ii), contains said liquid hydrocarbon compounds having at least five carbon atoms in an amount of at least 80% per total hydrocarbon fraction.

9. The method of claim 1, wherein said method is integrated with a fermentation process, wherein said fermentation process produces said alcohol as a component of a fermentation stream.

10. The method of claim 9, wherein said fermentation process produces said alcohol from a biomass source.

11. The method of claim 10, wherein said biomass source is comprised of lignocellulosic matter.

12. The method of claim 10, wherein said biomass source is comprised of starch or sugar.

13. The method of claim 1, wherein said method further comprises distilling said hydrocarbon fraction reduced in gaseous hydrocarbon content to obtain a refined hydrocarbon fraction.

14. The method of claim 1, wherein said first and second metal-loaded zeolite catalysts are V-ZSM-5.

* * * * *